(12) United States Patent
Lynn et al.

(10) Patent No.: US 6,342,039 B1
(45) Date of Patent: Jan. 29, 2002

(54) MICROPROCESSOR SYSTEM FOR THE SIMPLIFIED DIAGNOSIS OF SLEEP APNEA

(75) Inventors: Lawrence A. Lynn, 1775 Olentangy River Rd., Columbus, OH (US) 43212; Eric N. Lynn, Columbus, OH (US)

(73) Assignee: Lawrence A. Lynn, Columbus, OH (US)

( * ) Notice: Subject to any disclaimer, the term of this patent is extended or adjusted under 35 U.S.C. 154(b) by 0 days.

(21) Appl. No.: 09/409,264

(22) Filed: Sep. 30, 1999

Related U.S. Application Data

(63) Continuation-in-part of application No. 08/789,460, filed on Jan. 27, 1997, which is a continuation of application No. 08/391,811, filed on Feb. 21, 1995, now Pat. No. 5,605,151, which is a continuation of application No. 08/151,901, filed on Nov. 15, 1993, now Pat. No. 5,398,682, which is a continuation-in-part of application No. 08/931,976, filed on Aug. 19, 1992, now abandoned.

(60) Provisional application No. 60/052,438, filed on Jul. 14, 1997, and provisional application No. 60/052,439, filed on Jul. 19, 1997.

(51) Int. Cl.[7] .................................................. A61B 5/00
(52) U.S. Cl. ........................ 600/529; 600/538; 600/310; 600/300; 600/323
(58) Field of Search ................................ 600/529, 534, 600/538, 310, 300, 323

(56) References Cited

U.S. PATENT DOCUMENTS

| 4,365,636 A | 12/1982 | Baker ......................... 128/716 |
| 4,523,279 A | 6/1985 | Sperinde |

(List continued on next page.)

FOREIGN PATENT DOCUMENTS

| DE | 9 200 422 | 7/1992 |
| WO | 8 801 149 | 2/1988 |
| WO | 9 009 146 | 8/1990 |

OTHER PUBLICATIONS

Fletcher, et al., Rate of Oxyhemolglobin Desaturation in Obstructive versus Nonobstructive Apnea; Am Rev Respir Dis. 143:657–660, 1991.

Fletcher, et al., effect of Cardiac Output Reduction on rate of Desaturation in Obstructive Apnea; Chest, 99:452–456, 1991.

(List continued on next page.)

*Primary Examiner*—Robert L. Nasser
(74) *Attorney, Agent, or Firm*—Pillsbury Winthrop LLP Intellectual Property

(57) ABSTRACT

A method of evaluating a patient with sleep apnea includes monitoring a patient to produce at least one timed waveform of at least one physiologic parameter, identifying along the waveform a first waveform variation indicative of an apnea, identifying along the waveform a second waveform variation indicative of another apnea, determining the interval intermediate at least one portion of the first waveform variation and at least one portion of the second waveform, and assessing the severity of sleep apnea based on at least the determining. A device for determining the severity of sleep apnea comprises a monitor capable of generating a signal indicative of at least one physiologic parameter and a processor capable of processing the signal, the processor operating to generate a timed waveform of the parameter and to identify a plurality of sequential waveform variations indicative of a corresponding plurality of sequential apneas, the sequential waveform variations having temporal and spatial relationships between the waveform variations and along the waveform, the processor further operating to determine at least one of the temporal and the spatial relationships and displaying the determining so that the determining can be used to assess the severity of sleep apnea.

35 Claims, 16 Drawing Sheets

U.S. PATENT DOCUMENTS

| | | | |
|---|---|---|---|
| 4,630,614 A | 12/1986 | Atlas | 128/721 |
| 4,738,266 A | 4/1988 | Thatcher | 128/664 X |
| 4,757,824 A | 7/1988 | Chaumet | 128/716 |
| 4,765,340 A | 8/1988 | Sakai et al. | |
| 4,802,485 A | 2/1989 | Bowers et al. | |
| 5,199,424 A | 4/1993 | Sullivan | |
| 5,206,807 A | 4/1993 | Hatke | |
| 5,275,159 A | 1/1994 | Griebel | 128/716 |
| 5,335,654 A | 8/1994 | Rapoport | |
| 5,385,144 A | 1/1995 | Yamanishi et al. | 128/716 |
| 5,398,682 A | 3/1995 | Lynn | |
| 5,483,969 A | 1/1996 | Testerman | |
| 5,485,851 A | 1/1996 | Erickson | |
| 5,540,733 A | 7/1996 | Testerman | |
| 5,605,151 A | 2/1997 | Lynn | |
| 5,645,053 A | 7/1997 | Remmers | |
| 5,645,054 A | 7/1997 | Cotner | |
| 5,704,345 A | 1/1998 | Berthon-Jones | |
| 5,740,795 A | 4/1998 | Brydon | |
| 5,765,563 A * | 6/1998 | Vander Schaaf | 600/538 |
| 5,769,084 A | 6/1998 | Katz | |
| 5,803,066 A * | 9/1998 | Rapoport et al. | 600/538 |
| 5,827,179 A * | 10/1998 | Lichter et al. | 600/538 |
| 5,902,250 A | 5/1999 | Verrier | |

OTHER PUBLICATIONS

"Evaluation of Obstructive sleep Apnea in Singapore Using Computerized Polygraphic Monitoring" Tan and T.H. Koh, *Annals Academy of Medicine,* Mar. 1991, vol. 20, No. 2 pp. 196–200.

"Unattended CPAP Titration: Toward a smart Machine" G. Guilleminault, R. Stopha, L. Milea, J. Catiman, E. Kaitkawski.

Strohl et al. Oxygen Saturation During Breath Holding and During Apneas in Sleep, Chest, Feb. 1984; 85, No. 1; 181–186.

George et al. Identification of Qualification of Apneas by Computer–based Analysis of Oxygen Saturation, American Review of Respiratory Disease, 1988; 137: 1238–1240.

Slutsky et al. Quantification of Oxygen Saturation During Epiosodic Hypoxemia. American Review of Respiratory Disease, 1980; 121:893–895.

Gyulay et al. A Comparison of Clinical Assessment and Home Oximetry in the Diagnosis of Obstructive Sleep Apena. American Review of Respiratory Disease, 1993; 147: 50–53.

Pepin et al. Does Oximetry contribute to the Detection of Apneic Events? Mathematical. Processing of the $SaO_2$ Signal. Chest, May 1991; 99: 1151–1157.

Timms et al. oxygen Saturation by Oximetry: analysis By Microcomputer, Journal of Polysomographic Technology, Spring 1988: 13–21.

Rauscher et al. Computerized Detection of Respirtory Events During Sleep from Rapid Increases in Oxyhemoglobin Saturation. Lung, 1991; 169: 355–42.

Rauscher et al. Quantification of sleep–disordered breathing by computerized analysis of oximetry, heart rate, and snoring. Eur Respir J. Jun. 1991; 4: 655–659.

Hoffarth, et al "Beurteilung Pulsoximetrisch erfasster zklisheer . . . " and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: 229–232).

Aubry et al. A microcomputer system for monitoring and analyzing oxyhemoglobin saturation during sleep. Computer Programs in Biomedicine. 1984; 18: 227–234.

Fletcher, et al. The Rate of Fall of Arterial Oxyhemoglobin Saturation in Obstructive Sleep Apnea. Chest, 1989; 96: 717–722.

Griffiths, et al. A video system for investigating breathing during sleep. Thorad, 1991; 46: 136–140.

Hoch, et al. Oberprufung der Fruherkennungsmethode MESAM und biox 3700 zur erfassung schiafbezogener Atmungsregulationsstorungen bei jungen Mannern. Pheumologie, 1991; 45: 217–222 and translation.

Selmi, et al. Evaluation of Automatic Analysis of SC58, Airflow and Oxygen saturation signals in Patients with Sleep related Apneas, Chest, 1989; 96: 255–61.

Sanders, et al. Obstructive Sleep Apnea Treated by Independently Adjusted Inspiratory and Expiratory Positive Airway Pressures via Nasal Mask. Chest, 1990: 98: 317–24.

Senes et al. Utility of Nocturnal Home Oximetry for Case Finding in Patients with Suspected Sleep Apnea Hypopnea Syndrome, Annl Int Med, 1993; 119–449 53.

Svanborg, et al A Limited Diagnostic Investigation for Static Charge Sensitive Bed. Chest, 1990: 98: 1341–45.

Kirby, et al. Computer quantitation of saturation impairment time as an index of oxygenation during sleep Com Meth, 1992; 107–115.

Series, et al., Influence of Continuous Positive Airways Pressure on Sleep apnea–related Desaturation in Sleep Apnea Patients. Lung, 1992; 170: 281–290.

Guilleminault C. et al, Unattended CPaP TTTration: Toward a Smart Machine, May 20, Stanford University Sleep Research Center.

Svanborg, et al A Limited Diagnostic Investigation for Obstructive Sleep Apnea Syndrome: Oximetry and Static Charge Sensitive Bed. Chest, 1990; 98: 1341–45.

Hoch, et al. Uberprufung der Fruherkennungsmethode MESAM und Biox 3700 zur Erfassung schlafbezogener Atmmgsergulationsstorungen bei jungen Mannern. Pneumologie, 1991; 45: 217–222 (and translation).

Salmi, et al. Evaluation of Automatic analysis of SCSB, Airflow and Oxygen Saturation Signals in Patients with Sleep Related Apneas. Chest, 1989; 96: 255–61.

Aubry, et al. The $SaO_2/t$ Diagram as a Useful Means To Express Nocturnal Hypoxemia. Chest, 1989; 96: 1341–45.

Evans, et al. A microcomputer system for monitoring and analysing oxyhemolobin saturation during sleep. Computer Programs in Biomedicine, 1984; 18: 227–234.

Longobardo et al., Sleep Apnea Considered As a Control System Instability, 9/1982, Respiratory Physiology 50: 311–333.

M.H. Wilkinson, et al. Effect of venous ozygenation on arterial desaturation rate during repetitive apneas in lambs, Respiration Physiology 101 (1995) 321–331.

Steven M. Scharf, et al., Cardiovascular Effects of Periodic Occlusions of the Upper Airways in Dogs, American Review of Respiratory Disease, pp. 321–329.

U. Koehler, et al., Nocturnal Myocardinal Ischemia and Cardiac Arrhythmia in Patients with sleep Apnea with an without Coronary Heart Disease (1991) 69; 474–482.

Guilleminault et al., "Sleep Apnea Syndrome: Can It Induce Hemodynamic Changes?", Western Journal of Medicine, vol. 123, Jul. 1975, pp. 7–16.

* cited by examiner

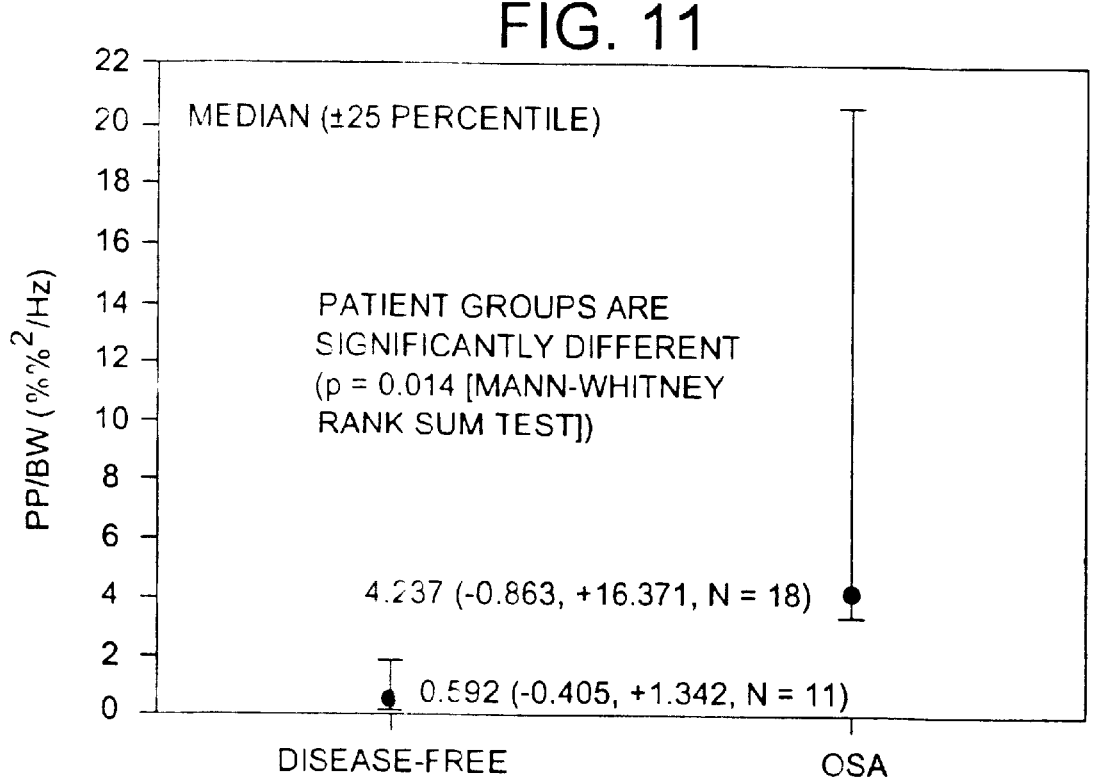
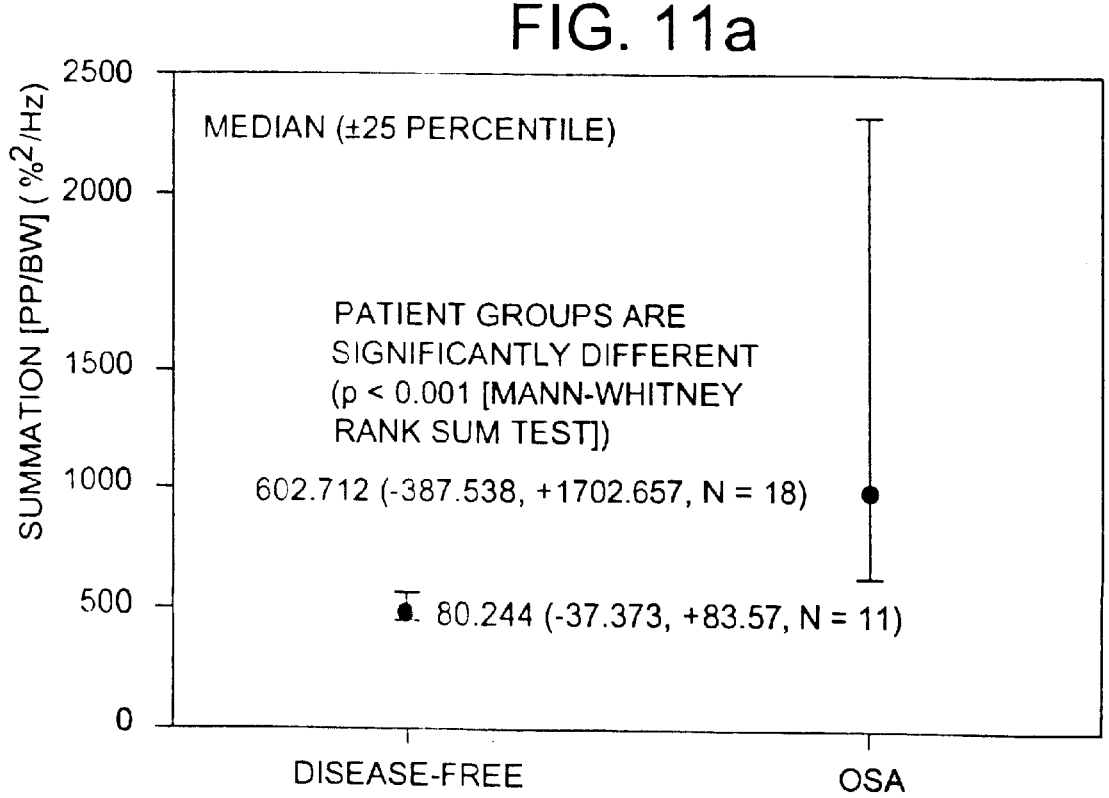

FIG. 15a

```
Public Sub Analyze(pnlMeter As Control)
    Dim lngPointCounter As Long
    Dim lngCasePointCount As Long
    Dim dblPreviousSaturation As Double
    Dim dblCurrentSaturation As Double
    Dim lng EventStartSequence As Long
    Dim lngCurrentDipoleSequence As Long
    Dim dplPrevious As CDipole
    Dim dplCurrent As CDipole
    Dim evtCurrent As CEvent
    Dim evtPrevious As CEvent
    Dim oscCurrent As COscillation
    Dim oscPrevious As COscillation If Not (cswcCase Is Nothing) Then
        'Set ccolDipoles = Nothing
        Set ccolDipoles = New Collection
        Set ccolEvents = Nothing
        Set ccolEvents = New Collection
        Set ccolOscillations = Nothing
        Set ccolOscillations = New Collection
        Set ccolOscillationPatterns = Nothing
        Set ccolOscillationPatterns = New Collection 'Define dipoles and events
        If cswcCase.PointCount > 1 Then
            Screen.MousePointer = vbHourglass
            dblPreviousSaturation = cswcCase.GetPoint(1)
            lngEventStartSequence = 1
            lngCasePointCount = cswcCase.PointCount For lngPointCounter = 2 To lngCasePointCount
                'Process meter if one was passed in.
                'If Not (pnlMeter Is Nothing) Then
                    'For speed optimization, only increment the meter
                    'every 1000 records.
                    If lngPointCounter Mod 1000 = 0 Then
                        pnlMeter.FloodPercent = lngPointCounter / lngCasePointCount * 100
                    End If
                'End If dblCurrentSaturation = cswcCase.GetPoint(lngPointCounter)
                Set dplCurrent = AddDipole(dblPreviousSaturation, dblCurrentSaturation)
                dblPreviousSaturation = dblCurrentSaturation 'Check for events
                lngCurrentDipoleSequence = lngPointCounter - 1
                If lngPointCounter > 2 Then
                    If dplPrevious.Polarity <> dplCurrent.Polarity Then
                        Set evtCurrent = NewEvent(lngEventStartSequence, lngCurrentDipoleSequence - 1)
                        AddIfQualified evtCurrent
                        lngEventStartSequence = lngCurrentDipoleSequence
                    End If
                End If Set dplPrevious = dplCurrent
```

FIG. 15b

```
Next
'Check to see if we have a final event
Set evtCurrent = NewEvent(lngEventStartSequence,
    lngCurrentDipoleSequence -1)
AddIfQualified evtCurrent
Screen.MousePointer = vbDefault
End If 'Identify oscillations
Set evtPrevious = Nothing
For Each evtCurrent In ccolEvents
    If Not (evtPrevious Is Nothing) Then
        If evtCurrent.StartDipoleSequence - evtPrevious.EndDipoleSequence + 1 _
            <= clngPositiveOscillationInterval And_
            evtPrevious.EventType = eevtSaturation And_
            evtCurrent.EventType = eevtDesaturation Then 'Add Positive Oscillation
            AddOscillation evtPrevious, evtCurrent ElseIf evtCurrent.StartDipoleSequence - evtPrevious.EndDipoleSequence + 1 _
            <= clngNegativeOscillationInterval And_
            evtPrevious.EventType = eevtDesaturation And_
            evtCurrent.EventType = eevtSaturation Then 'Add Negative Oscillation
            AddOscillation evtPrevious, evtCurrent End If
    End If
    Set evtPrevious = evtCurrent
Next 'Identify oscillation patterns
Set oscPrevious = Nothing
For Each oscCurrent In ccolOscillations
    If Not (oscPrevious Is Nothing) Then
        If oscCurrent.FirstEvent.StartDipoleSequence - oscPrevious.
            SecondEvent.EndDipoleSequence + 1_
            <=clngBipolarOscillationPatternInterval And_
            oscPrevious.OscillationType = eoscNegative And_
            oscCurrent.OscillationType = eoscPositive Then 'Add Positive Oscillation
            AddOscillationPattern oscPrevious, oscCurrent E1self oscCurrent.FirstEvent.StartDipoleSequence - oscPrevious.
            SecondEvent.EndDipoleSequence + 1_
            <= clngCoupledOscillationPatternInterval And_
            oscPrevious.OscillationType = eoscNegative And_
            oscCurrent.OscillationType = eoscNegativeThen 'Add Negative Oscillation AddOscillationPattern oscPrevious, oscCurrent End If
    End If
    Set oscPrevious = oscCurrent
Next End Sub
```

MICROPROCESSOR SYSTEM FOR THE SIMPLIFIED DIAGNOSIS OF SLEEP APNEA

RELATED APPLICATIONS

This application claims the benefit of U.S. Provisional Application No. 60/052,438, filed Jul. 14, 1997, the contents of which are hereby incorporated herein by reference and the benefit of U.S. Provisional Application No. 60/052,439, filed Jul. 14, 1997, the contents of which are hereby incorporated herein by reference. This application is a continuation-in-part of U.S. application Ser. No. 08/789,460, filed Jan. 27, 1997, which is a continuation of U.S. patent application Ser. No. 08/391,811, filed Feb. 21, 1995, now U.S. Pat. No. 5,605,151, which is a continuation of U.S. patent application Ser. No. 08/151,901 filed Nov. 15, 1993, now U.S. Pat. No. 5,398,682, which is a continuation-in-part of U.S. patent appln. Ser. No. 08/931,976, filed Aug. 19, 1992, now abandoned the contents of application Ser. Nos. 08/789,460, 08/391,811, 08/151,901, 08/931,976 and PCT/US 93/97726, and of U.S. Pat. Nos. 5,605,151 and 5,398,682 are all hereby incorporated herein by reference. The contents of which are incorporated herein by reference.

BACKGROUND AND SUMMARY OF THE INVENTION

Obstructive Sleep Apnea is now recognized as one of the most common disorders in the U.S. The lower oxygen levels associated with Obstructive Sleep Apnea is now known to be a major cause of cardiovascular morbidity including heart attack and stroke. A crisis exists in the U.S. in that traditional expensive polysomnography cannot be used to identify these patients on a sufficient scale. The situation is analogous to having disease as common and subtle as insulin dependent diabetes without an inexpensive and widely implementable and simple mechanism to diagnose the disorder (such as exists for diabetes). Millions of patients remain undiagnosed. The development of a diagnostic system which can allow simplified diagnosis of obstructive sleep apnea by the primary care physician is a national healthcare priority of substantial scale. The prevention of hundreds of thousands of annual excess deaths, stroke and heart attacks associated with obstructive sleep apnea through simplified recognition of this disorder is the most important purpose of the present invention. These excess deaths are occurring annually in a great part due to the lack of availability of this technology resulting in a vast pool of undiagnosed cases of Sleep Apnea. Despite the fact that obstructive sleep apnea is easily treated, both the patient and the family are often completely unaware of the presence of this dangerous disease, thinking the patient just a "heavy snorer".

Obstructive sleep apnea often develops insidiously as a patient enters middle age and begins to snore. The major cause is an increase in fat deposition (often age related) in the neck which results in narrowing of the airway. (In fact the probability that a 40 year old has sleep apnea is directly related to his or her neck circumference). When the muscle tone of the upper airway diminishes during sleep and negative pressure associated with inspiration through this somewhat narrow airway results in collapse of the upper airway in a manner analogous to the collapse of a cellophane straw. This results in airway obstruction and, effectively chokes off all air movement. The choking patient (still asleep) begins to struggle and inhales more forcibly, thereby, further lowering upper airway pressure and causing further collapse of the upper airway. During this time, substantially no air movement into the chest occurs and the patient experiences a progressively fall in oxygen (similar to the fall occurring early in drowning). The fall in oxygen produce central nervous system stimulation contributing to hypertension and potential heart and blood vessel injury and finally results in arousal. Upon arousal, increase in airway muscle tone opens the airway and the patient rapidly inhales and ventilates quickly to correct the low oxygen levels. Generally, the arousal is brief and the patient is not aware of the arousal (or of the choking since this occurs during sleep). Once oxygen levels have been restored, the patient begins again to sleep more deeply, upper airway tone again diminishes, the upper airway collapses and the cycle is repeated stressing the heart with low oxygen in a repetitive fashion. Often this repeating cycle over many years eventually results in damage to the heart muscle and/or the coronary arteries. As the patient ages, the consequences of undiagnosed obstructive sleep apnea is often either a progressive decline in heart muscle function (and eventual heart failure) or heart infarction.

The duration and severity of each apnea is quite variable from patient to patient and with the same patient throughout the night. Indeed, the disease process represents a spectrum of severity from mild snoring, which is associated with incomplete and inconsequential airway obstruction, to severe apneas, which can result in fatal hypoxemia.

This disease commonly results in excessive daytime sleepiness and can disrupt cognitive function during the day due to fragmentation of sleep during the night associated with recurrent arousals of which the patient is not aware.

Although this disease commonly affects obese patients, it may occur in patients with any body habitus. Because this disease is so common and because it presents with the subtle and common symptoms of excessive daytime sleepiness, morning headache, and decreasing ability to concentrate during the day, it is critical that an inexpensive technique for accurately diagnosing and treating this disease be developed. Traditionally, this disease has been diagnosed utilizing a complex and expensive multichannel polysomnogram. This is generally performed in a sleep lab and involves the continuous and simultaneous measurement and recording of an encephalogram, electromyogram, extraoculogram, chest wall plethysmogram, electrocardiogram, measurements of nasal and oral airflow, and pulse oximetry. These, and often other channels are measured simultaneously throughout the night and these complex recordings are then analyzed to determine the presence or absence of sleep apnea.

The problem with this traditional approach is that such complex sleep testing costs between one thousand to thirty five hundred dollars. Since sleep apnea is so common, the cost of diagnosing obstructive sleep apnea in every patient having this disease in the United States would exceed Ten Billion Dollars. It is critical that a new, inexpensive technique of accurately diagnosing sleep apnea be developed.

Nocturnal oximetry alone has been used as a screening tool to screen patients with symptoms suggestive of sleep apnea to identify whether or not oxygen desaturations of hemoglobin occur. Microprocessors have been used to summarize nocturnal oximetry recordings and to calculate the percentage of time spent below certain values of oxygen saturation. However, oxygen desaturation of hemoglobin can be caused by artifact, hypoventilation or ventilation perfusion mismatching. For these reasons, such desaturations identified on nocturnal oximetry are not specific for sleep apnea and the diagnosis of sleep apnea has generally required extensive formal polysomnography.

The present invention comprises a system and technique for deriving and utilizing the analysis of graphical pulse oximetry-derived waveforms as a function of time to accurately diagnose sleep apnea with adequate specificity to, in many cases, eliminate the need for expensive formal polysomnography.

It is the purpose of this invention to provide an inexpensive system for the collection and analysis of pulse oximetry values as a function of time during sleep to provide a diagnosis of sleep apnea with a high degree of specificity.

This invention provides a reliable and specific means for the diagnosis of obstructive sleep apnea, which can be performed in the patient's home without attendance of technical personnel. It is further the purpose of this invention to provide an inexpensive and accurate means to both screen for and specifically diagnose obstructive sleep apnea by a single overnight recording in the patient's home without the need for multiple connections to different parts of the patient's body. It is further the purpose of this invention to define a technique for diagnosing obstructive sleep apnea utilizing the calculation of the ascending and descending slope ratio of phasic oxygen desaturations measured during sleep.

Specifically, the present invention defines a device for diagnosing sleep apnea that has the following components. First, a means must determine an oxygen saturation of a patient's blood. This saturation value is coupled to a means for identifying a desaturation event based on the saturation value. The desaturation event is one in which said oxygen saturation falls below a baseline level by a predetermined amount and for a predetermined time. The slope of the event is calculated by means for calculating a slope of said desaturation event representing a rate of change per unit time of fall of oxygen saturation. This slope is used by a means for comparing said calculated slope with a value of slope which is determined in advance to be indicative of sleep apnea, and determination of diagnosis of sleep apnea is made based on said comparing.

The comparing can be done by:
1) comparing with an absolute number which is likely to indicate a sleep apnea, or
2) comparing with other slopes taken at different times.

The identifying means can also identify a resaturation, immediately following said desaturation and coupled with said desaturation, in which the oxygen saturation rises, and wherein the determination can also be based on a slope of said resaturation.

Many other ways of calculating the slope are also disclosed herein.

These and other aspects of the invention will now be described in detail with reference to the accompanying drawings, wherein:

BRIEF DESCRIPTION OF THE DRAWINGS

Table 1 illustrates the sequence of respiratory drive cycles which induces a cluster waveform indicative of sleep apnea.

FIG. 11 shows a plot comparing disease free patients with patients having a diagnosis of obstructive sleep apnea.

FIGS. 15a and 15b is one preferred listing of an object oriented programming code according to the present invention.

DESCRIPTION OF THE PREFERRED EMBODIMENTS

Figure 1:
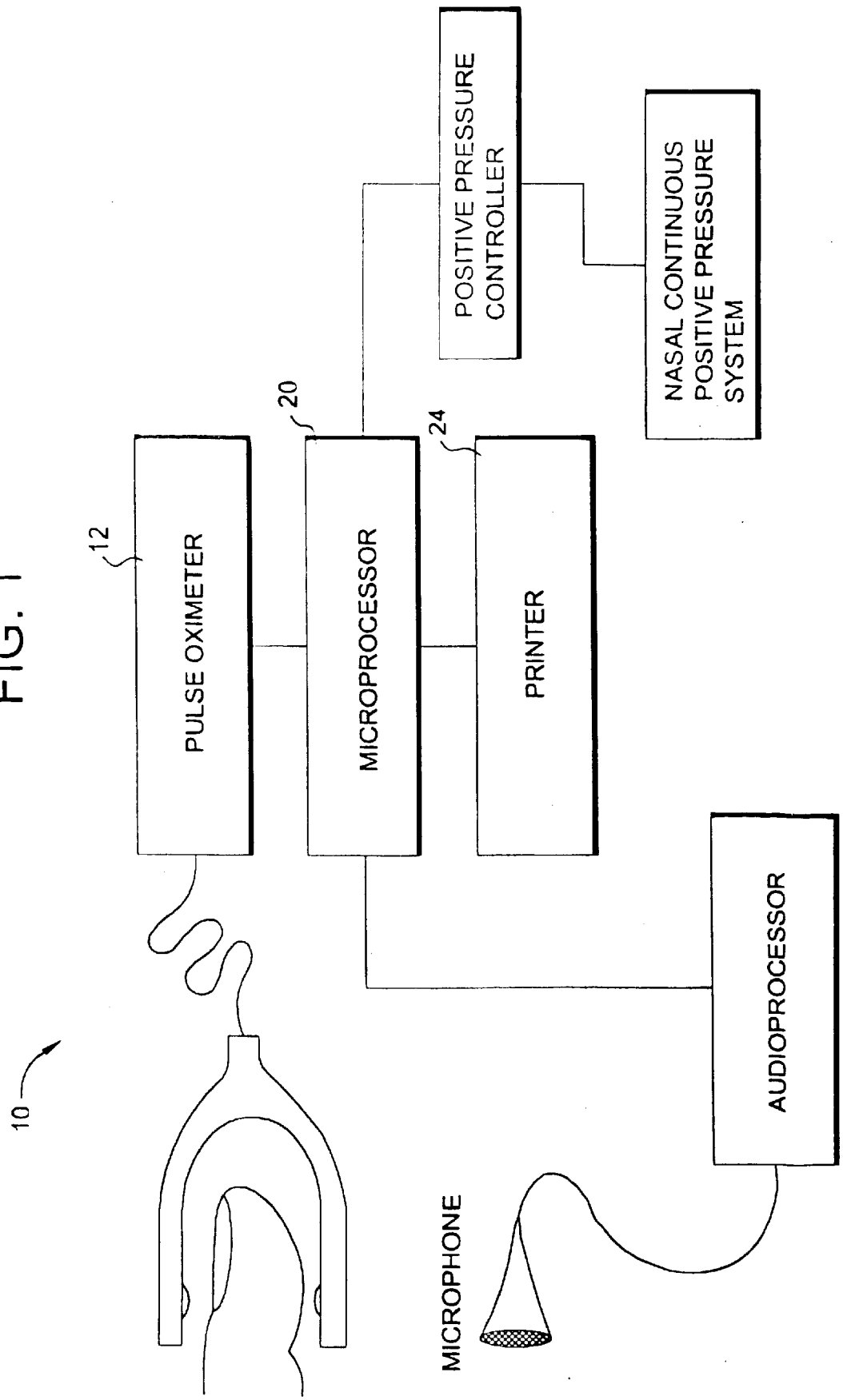
FIG. 1 shows a block diagram of the basic system of the present invention.

The inventor of the present invention found, relative to sleep apnea diagnosis, that the waveform pattern of oximetry during a sleep recording could be considered in relation to the physiologic parameters, which affect oxygen saturation over time. Specifically, during an apneic period, arterial oxygen saturation initially falls as a function of the oxygen saturation of mixed venous blood and oxygen uptake from residual exchangeable oxygen within the lungs. Subsequently, arterial oxygen saturation falls directly as a function of oxygen consumption and global oxygen stores. These stores of oxygen are very limited. The sources of oxygen available during an apneic period include residual exchangeable oxygen within alveoli and airways; the oxygen bound to hemoglobin, dissolved oxygen within body tissues and oxygen stored as myoglobin. These stores are rapidly depleted during an apneic period as a function of global oxygen consumption. As oxygen stores are depleted, the cellular oxygen levels fall, and mixed venous oxygen saturation progressively diminishes. Since a small amount of exchangeable oxygen supply exists within alveoli and airways, arterial oxygen saturation, as measured by the pulse oximeter is briefly unaffected by the initial fall in body oxygen storage. However, since oxygen stores within the alveoli are extremely limited, arterial oxygen saturation then progressively falls toward that of mixed venous arterial blood saturation since little significant gas exchange occurs as mixed venous blood passes by essentially unventilated alveoli. The partial pressure of oxygen in arterial blood therefore progressively falls toward the mean partial pressure of oxygen in body tissues at the cellular level.

It is possible to measure indirectly the partial pressure of oxygen in arterial blood by measurement of arterial oxygen saturation of hemoglobin utilizing a pulse oximeter 12. If the probe 13 of the pulse oximeter is placed on a patient's finger or other body part during a prolonged apneic period, a progressive decrement in arterial saturation will be identified as a function of the fall in arterial oxygen partial pressure. Although the initial decline in arterial oxygen saturation is greatly dependent on mixed venous oxygen saturation, since body oxygen stores during an apnea cannot be repleted, the subsequent portion of the fall in arterial oxygen saturation as measured by a pulse oximeter over time will be directly correlated to the oxygen consumption of a resting human (approx. 3.5 ml/kg/min) has a relatively constant relationship to average body arterial oxygen stores (approx. 25 ml/kg). Although substantial variability exists in body oxygen stores in chronically ill patients with low cardiac output states (resulting in lower mixed venous oxygen storage), a finite range of oxygen stores exists. Indeed, even in the presence of sever compensated disease, mixed venous oxygen saturation initially and of oxygen consumption and body oxygen stores terminally. Although augmented body muscular activity associated with obstructive apnea could modestly increase oxygen consumption and although a decrease in oxygen consumption may occur below a critical level of tissue oxygenation, the declining range of slope of desaturation is still predictable within only modest variances.

To understand the predictable parameters of arterial pulse oximetry waveform, it is important to consider the way in which pulse oximetry reflects total body oxygen stores. Total body oxygen stores can be conceived as representing four major compartments: the Lung Compartment, the Arterial Compartment, the Tissue Compartment, and the Venous Compartment Oxygen enters the lungs and is stored sequentially in each of these compartments. When oxygen is depleted during apnea, depletion occurs first in the tissue compartment, second in the venous compartment, third in the lung compartment, and fourth in the arterial compartment. Whereas, when oxygen is repleted, oxygen appears first in the lung compartment, second in the arterial compartment, third in the lung compartment, and fourth in the venous compartment. It can be seen, therefore, that since pulse oximetry measurements reflect oxygen stored within the arterial compartment, if sequential depletion of arterial saturation occurred due to phasic apneas that the initial apneic episode would result in depletion of the arterial compartment only after the substantial depletion of other compartments has developed.

Using the above, the inventor of the present invention realized that he could predict with reasonable certainty whether or not a desaturation occurring during a continuous nocturnal oximetry measurement falls within the anticipated range of parameters which define the slope of arterial oxygen desaturation of hemoglobin which can physiologically occur during an apneic episode. In this manner, each desaturation episode can be defined, as a function of the characteristics of the waveforms of deflection, as either consistent with an apneic episode or inconsistent with an apneic episode. Saturations which decrease too rapidly to be accounted for on the basis of physiologic oxygen depletion due to apnea, would be identified as inconsistent with an apneic episode and therefore identified as being secondary to artifact. On the other hand, the desaturation episodes which decrease too slowly to be accounted for on the basis of physiologic oxygen depletion and would be identified as inconsistent with an apneic episode and therefore secondary to either hypoventilation, alterations in ventilation perfusion matching, or to artifact. The means for identifying a desaturation event is preferably a processor; and according to the above, the processor compares a calculated slope of the event with a value of slope which is determined in advance to be indicative of sleep apnea. A diagnosis of sleep apnea is made based on that comparison.

More specifically, the preferred embodiment of the sleep apnea diagnosis system 10 of the present invention is shown in FIG. 1. It includes a conventional pulse oximeter 12 with a probe 14 for transillumination or reflection from a human body part such as a finger 16. The oximeter is connected to a microprocessor 20, which records oxygen saturation and pulse as a function of time. A printer 24 is connected to the microprocessor. The microprocessor analyzes the oxygen saturation values as a function of time as will be discussed in detain herein. In one preferred embodiment, the system is used in the following way:

The microprocessor is disposed in connection with the oximeter with a probe and printer for recording the oxygen saturation as a function of time, and the oximeter probe is attached to a patient. The oxygen saturation of hemoglobin is recorded as a function of time while the patient sleeps.

Figure 2:
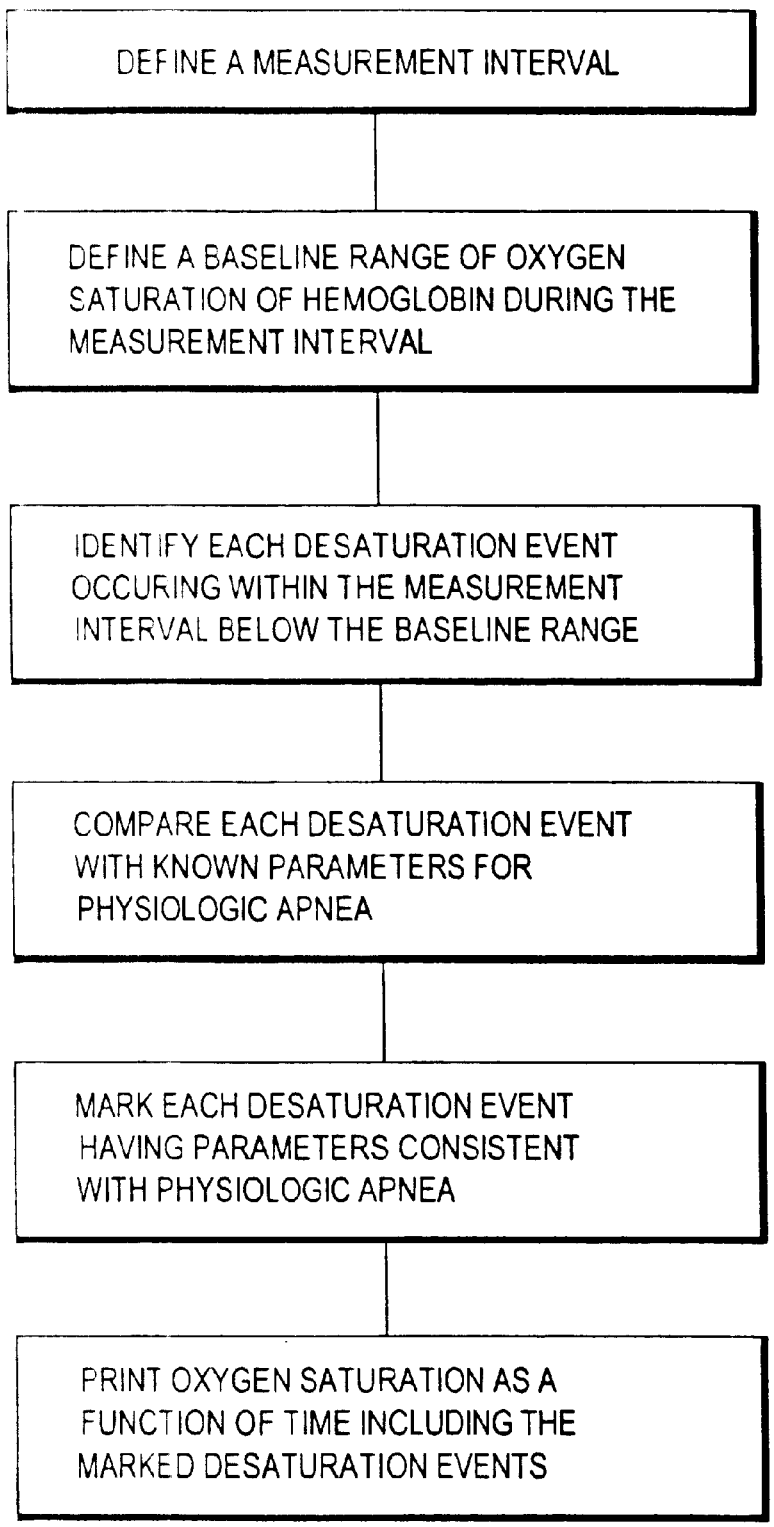
FIG. 2 shows a basic flowchart of operation of the present invention.

A measurement interval of, for example, 10 minutes is defined along the sleep recording is shown in step 200 of FIG. 2. Step 202 defines a mean maximum baseline range of oxygen saturation of hemoglobin ($\pm 3\%$ saturation) is defined over the measurement interval.

A desaturation event can be defined as at least a 4% substantially uninterrupted decrement in saturation below the defined baseline mean of oxygen saturation. A lower percentage can be used to increase sensitivity. Each desaturation event is identified in step 204, and the desaturation change of each desaturation event is measured. The desaturation interval I defined as the duration of the uninterrupted decline in saturation of each desaturation event.

Then, slopes are calculated. The descending slope of each desaturation event is calculated as:

$$\Delta S_D / \Delta T_D$$

Where:
$\Delta S_D$=Desaturation change (in % saturation)
$\Delta T_D$=Desaturation interval (in seconds)

A resurrection event is defined as a substantially uninterrupted rise in saturation, which terminates the declining slope of desaturation event. The resaturation change of each resaturation event is also measured.

The resaturation interval is measured as the duration of the uninterrupted rise in saturation of each resaturation event. The ascending slope of each resaturation event is calculated as:

$$\Delta S_R / \Delta T_R$$

Where:
$\Delta S_R$=Desaturation change (in % saturation)
$\Delta T_R$=Desaturation interval (in seconds)

A phasic desaturation event is defined using all coupled desaturation and resaturation events wherein the sum of the duration of the desaturation event and the resaturation event is less than 3.5 minutes and wherein the descending slope falls within a finite range of between 1.4%/sec and 0.3%/sec.

The descending to ascending saturation slope ratio of each phasic desaturation event is calculated as:

$$(\Delta S_D / \Delta T_D) / (\Delta S_R / \Delta T_R)$$

The number of probable apneic events within the measurement interval is defined as the number of phasic desaturation events falling within the finite range of ascending to descending slope ratios of between 3.5–10.5.

Each probable apneic event is marked with the identity marker, PA, and the above steps are repeated for each additional 10 min. interval along the recording for the entire sleep recording.

Then, appropriate action is taken: either the pulse oximetry waveform is printed as a function of time with each probable apneic event marked PA for identification, or treatment of sleep apnea is either manually or automatically administered.

The probability that a patient has sleep apnea will be a direct function of the number of phasic desaturations, which meet the above criteria for sleep apnea per hour of recording and this probability, can be calculated and printed.

Figure 4:
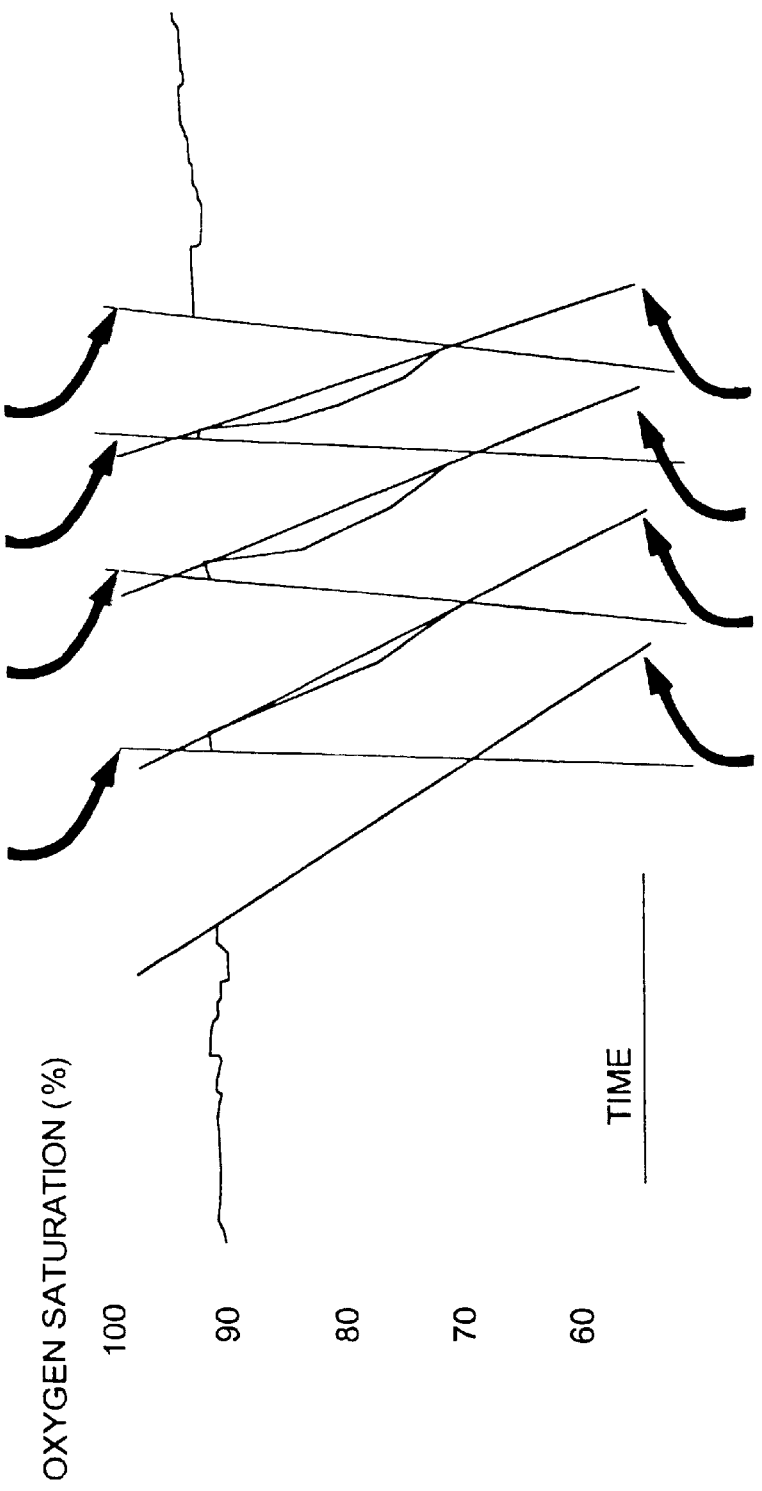

Therefore, in the preferred embodiment, each desaturation event is identified as to whether or not it meets the criteria for physiologic apnea. The number of events per hour are then calculated and then printed. Each desaturation event which has been identified by the microprocessor as consistent with a physiologic apnea is so marked (such as PA for probable apnea or PCA for physiologically consistent with apnea). The pulse oximetry waveform in the preferred embodiment is then printed to provide a hard copy. This printed hard copy includes identification of each desaturation event, which has been determined by the microprocessor as consistent with a physiologic apnea. In addition, the presence of desaturation slope acceleration, as will be discussed, by comparing closely spaced consecutive desaturation slopes as in FIG. 4 and such identification also provided on the printed hard copy.

This invention therefore provides a compact, single device which is easily suitable for home use and can be simply taken home by the patient and interfaced with a body part such as a finger, to provide both screening and a mechanism to provide a specific diagnosis of sleep apnea with a single overnight recording. The hard printed copy provides graphical data which can be overread by the physician since the computer specifically identifies the desaturation events which have been interpreted as consistent with sleep apnea. This provides the physician with the opportunity to determine whether he or she agrees with the diagnostic interpretation of the microprocessor.

The diagnosis can be treated by repeating the sleep recording during nasal CPAP (Continuous Positive Airway Pressure) therapy. The identifications of multiple desaturations with patterns as defined above which are consistent with the physiology of apnea and which are eliminated by nasal CPAP therapy is diagnostic of apnea and further establishes the parameters defining effective treatment requirements.

The invention includes the system taking additional action based on the identification of the diagnosis of sleep apnea based on the above slope comparison. The action can include, as in FIG. 1, the microprocessor activating a range of nasal continuous airway pressures through a pressure controller within defined limits to automatically and effectively treat a patient's sleep apnea once the diagnosis of sleep apnea has been made by the microprocessor. Activation of flow is initiated by the microprocessor on identification of multiple sleep apnea-related desaturations meeting the criteria as described above. The pressure can be titrated upward by, for example 1–2 cm $H_2O$ pressure increments by the microprocessor upon identification of multiple consecutive desaturations which are not effectively eliminated by the starting pressure.

In this way, the invention greatly enhances the diagnostic sensitivity and specificity of nocturnal oximetry in the diagnosis of sleep apnea and to further utilize the identification of oximetry derived desaturation events to trigger the storage and/or collection of additional sensory data concerning each desaturation event and; furthermore the system can be utilized to automatically initiate and adjust therapy to mitigate further after following desaturation events.

In addition to a definable descending desaturation slope, oximetry measurements during apnea periods have other definable and predictable parameters. Importantly, apneic episodes have a definable and predictable range of duration. It is clear that brief apneic episodes, for example with breath holding does not result in significant arterial oxygen desaturation as measured by pulse oximetry. However, when apneic periods are prolonged as with obstructive sleep apnea, oxygen desaturation progressively declines as a function of factors, as previously discussed. Unless such an apneic episode is limited in duration, the patient would die from hypoxemia. Therefore, each desaturation which occurs as a function of apnea will have a phasic quality with a predictable range of duration. A second aspect of the invention analyzes the duration of the apneic episode to determine if it is of duration of the apneic episode to determine if it is of a duration likely to indicate sleep apnea.

The range of duration generally does not exceed three minutes. Therefore, for a desaturation event identified by pulse oximetry to be secondary to an apneic episode, it should preferably have a duration of less than three minutes. Oxygen desaturations due to sleep apnea should be terminated with the resaturation of recovery within 3–3.5 minutes or less. Oxygen desaturation events, which occur for greater than three minutes are, identified as either secondary to hypoventilation, ventilation perfusion mismatching, or artifact.

Another aspect of the invention is based on the recognition that an apneic episode which occurs during sleep is generally reversed by an arousal. At this point, the patient's central nervous system increases upper airway tone and atmospheric gas rapidly enters the lungs and exchanges with the oxygen-depleted gas within the alveoli. This exchange occurs within a few seconds. Since mixed venous blood in pulmonary capillaries rapidly equilibrates with the partial pressure of oxygen in the alveoli, arterial oxygenation will recover within seconds of the repletion of oxygen within alveoli. It should be noted that the amount of time required for blood to pass from the pulmonary capillaries to the peripheral site of pulse oximetry measurement can be measured is very brief. Therefore, the ascending slope of oxygen saturation during recovery from an apneic episode is extremely rapid. Ascending slopes which are not rapid are unlikely to be secondary to repletion of oxygen partial pressure within alveoli associated with arousal from an apneic episode and rather may be secondary to a crescendo of increasing respirations following a hypoventilation episode as in Cheyne-Stokes respirations or may be secondary to improvement in ventilation perfusion matching. In a recent study performed by the present inventor the mean slope of desaturation was 0.8% per second, with all desaturation slopes ranging between 0.3% per second and 1.1% per second. The mean slope of recovery 7.6% per second, with recovery slopes ranging from 2.5% per second to 8.3% per second. The mean recovery to apnea slope ratio was 7.66, with a range of 3.8 to 10.4. Hence, in yet another aspect of the invention, the resaturation slope, immediately following the desaturation, is also determined, and used in the diagnosis of sleep apnea.

Additional ways of comparing the calculated slope with a value of slope which is determined in advance to be indicative of sleep apnea include using other parameters to enhance the specificity of continuous nocturnal oximetry in the diagnosis of sleep apnea include comparisons of consecutive desaturation slope values and the identification of alterations in desaturation values as a function of events occurring immediately prior to the desaturation event.

Since obstructive sleep apnea events occur by similar physiologic process each time within the same patient, consecutive desaturation events will commonly have similar desaturation slopes. The identification of these consecutive desaturation events having similar desaturation slopes which have values consistent with physiologic apnea provides additional evidence supporting these events as secondary to cyclic obstructive sleep apnea.

Furthermore, the preceding desaturation event can effect the shape and the slope of the desaturation event, which immediately follows. That is, preceding desaturation event may accelerate the initial portion of the slope of the following desaturation. Although other factors may contribute to the development of this increase desaturation slope, the primary factor appears to be the depletion of body oxygen stores where insufficient time has developed for repletion for tissue and venous oxygen stores. However, the pulse oximeter is measuring arterial oxygen saturation. Therefore, after repletion of oxygen stores within the lung, arterial oxygen saturation rapidly rises before venous oxygen stores have been repleted. If an apneic event recurs before the restoration of venous oxygen stores, this apneic event will be superimposed upon substantially depleted total body oxygen stores, this apneic event will be superimposed upon substantially depleted total body oxygen stores despite the fact that pulse oximetry may demonstrate normal arterial oxygen saturation. Since at this time apnea is occurring in the presence of markedly depleted body oxygen stores (i.e. a much lower mixed venous oxygen saturation), the initial portion of the slope of the declining arterial oxygen saturation may be substantially greater that the slope of the decline of oxygen saturation which occurred during the preceding desaturation event. This phenomenon would not be expected to occur in association with artifact and would only be expected to occur in the presence of rapidly cycling changes in body tissue oxygen stores. Consecutive closely spaced desaturation events, therefore, interact so that the first desaturation event can affect the waveform of the second desaturation event provided the interval between the two events is short enough and the level of the desaturation occurring in the first event is substantial enough to result in a sizable depletion of total body oxygen stores.

The greatest portion of oxygen storage is within the venous compartment. At any given time, therefore, the amount of global oxygen stored, is in large part, a function of the extent of excess of oxygen delivered to the tissues which is stored within the venous pool. In the absence of arterial hypoxemia or profoundly compromised cardiovascular function, oxygen delivery substantially exceeds oxygen demand, resulting in considerable oxygen stores within the mixed venous pool. The amount of oxygen stored within the mixed vellous pool can, therefore, be seen as a dynamically stored, hidden buffer which mitigates the decline in saturation attendant any change in alveolar ventilation. Although patients with profoundly decreased mixed venous oxygen saturations would be expected to have a more rapid and greater fall in arterial oxygen saturation for any given level of change in alveolar ventilation, this still falls within a definable range.

During very rapidly cycling apneas (i.e. apneas occurring within less than 10–20 seconds of each other), body oxygen stores can be seen therefore as a moving wave through consecutive body compartments wherein the first wave affects the configuration of the second wave. The identification of this effect should be virtually diagnostic of rapidly cycling sleep apnea and this phenomenon can be exploited to assist in the specific diagnosis of sleep apnea utilizing the recording of nocturnal oximetry alone.

Desaturation slope acceleration may occur when cycling apneic events occur within less than 10 seconds of each other and when the depth of arterial saturation associated with the first cyclic event is greater than 15%. The inter-desaturation event intervals can be defined specifically as that point wherein the first desaturation event recovers substantially to baseline to the point in time when the second desaturation event begins to decline from the baseline.

It can be seen, therefore, that a declining waveform of arterial oxygen desaturation in severe sleep apnea can be expected to have two major physiologically-derived components: 1) the slope of the initial declining limb which is primarily a function of the level of mixed venous oxygen saturation at the onset of apnea and the amount of exchangeable oxygen in the lung remaining after the onset of apnea. 2) the second component or terminal limb is primarily a function of global oxygen consumption relative to body oxygen stores. (The terminal limb may not be present if apnea is brief.) The slope of the initial and terminal limb are generally similar in patients with normal mixed venous oxygen saturations. However, in patients with significantly low mixed venous oxygen saturation, the initial limb, producing an angled appearance suggesting antecedent depletion of mixed oxygen stores.

The magnitude of the oxygen deficit which is derived from the preceding apneic event less the intervening excess oxygen uptake which attenuates this deficit between the apneas defines the magnitude of the slope acceleration of the initial limb of the after-following desaturation event. Therefore, an interval of oxygen deficit is present following a sustained apnea but it is hidden since arterial oxygen saturation is normal.

Figure 3:
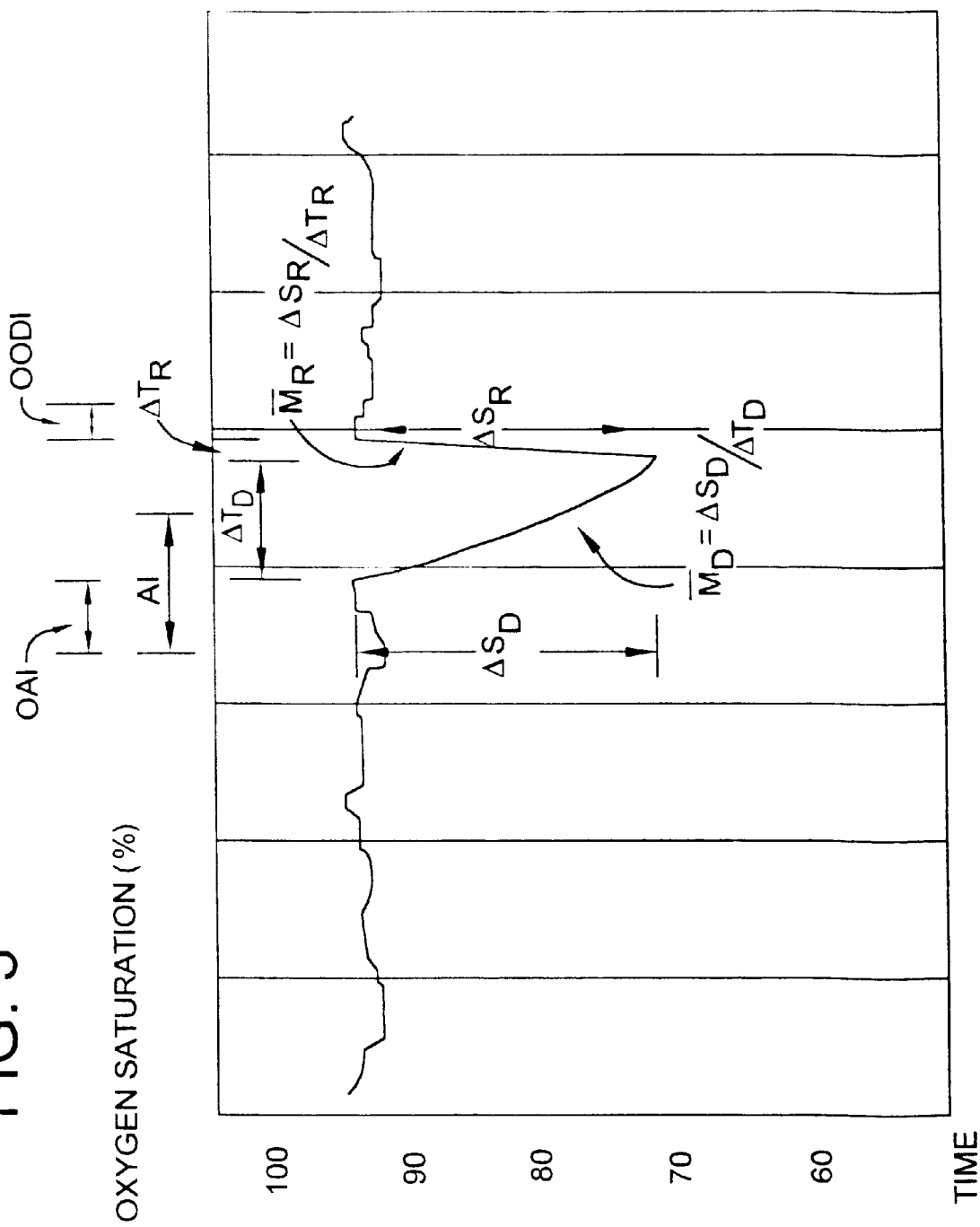
FIGS. 3 and 4 show basic desaturation events and many of the parameters associated therewith.

FIG. 3 illustrates a desaturation event and many of the parameters as discussed supra which define the event. The parameters shown include:

$\Delta S_D$=Fall in saturation (in % sat.)

$\Delta S_R$=Rise in saturation (in % sat.)

$\Delta T_D$=Duration of the fall in Saturation/desaturation (in seconds)

$\Delta T_R$=Duration of the rise in saturation/resaturation (in seconds)

$M_D = \Delta S_D/\Delta T_D$=Mean slope of Desaturation $M_D = \Delta S_D/\Delta T_D$=Mean slope of Restoration $M_D = \Delta S_D/\Delta T_D$=Mean slope of Restoration We also define the following terms:

AI (the apnea interval)—The actual time wherein the patient experiences cessation of airflow which precipitates oxygen desaturation.

OAI (the occult apnea interval)—The interval wherein apnea has occurred; however, arterial oxygen stores are maintained by a shift of oxygen stores from the lung and venous compartment into the arterial compartment into the arterial compartment hiding the fall in body oxygen stores with respect to the oximetry measurement.

OODI (the occult oxygen deficit interval)—The interval immediately following return of oxygen saturation to near baseline after a desaturation event and wherein mixed venous oxygen desaturation persists. If a second apnea occurs within this interval, the slope of desaturation may be increased.

Using these parameters and realizations discussed supra, the inventor of the present invention made a system and technique which automatically analyzed the waveform pattern of continuous nocturnal oximetry, to specifically identify the presence or absence of moderate to severe obstructive sleep apnea-induced arterial oxygen desaturation. Such a system and technique makes it possible to diagnose moderate to severe obstructive sleep apnea with confidence with a single channel recording of nocturnal oximetry alone avoiding the need for complex and expensive polysomnography in the diagnosis of this disorder. The system and technique includes a mechanism to achieve the measurement of a compendium of parameters, which are repetitively measured and analyzed, each improving the specificity of the diagnosis.

A summary of one such technique is as follows:

1. Dispose a microprocessor in connection with the oximeter with a probe and printer for recording the oxygen with a probe and printer for recording the oxygen saturation of hemoglobin as a function of time.
2. Attach the oximeter probe to a patient.
3. Define a measurement interval.
4. Define the mean baseline event as at a specific uninterrupted decrement in saturation below the defined baseline range of oxygen saturation.
5. Define a desaturation event as at a specific uninterrupted decrement in saturation below the defined baseline range of oxygen saturation.
6. Measure the duration of the uninterrupted decline in saturation of each desaturation event.
7. Calculate the descending slope of each desaturation event.
8. Define a resaturation event as an uninterrupted rise in saturation, which terminates the declining slope of the desaturation event.
9. Calculate the ascending slope of each resaturation event.
10. Define a phasic desaturation event as all coupled desaturation and resaturation events wherein the sum of the duration of the desaturation event and the resaturation event is less than a specified value and wherein the descending slope falls within a finite range.
11. Calculate the descending to ascending saturation slope ratio of each phasic desaturation event.
12. Define the number of probable apneic events within the measurement interval by comparing said calculated slope with a value of slope which is determined in advance to be indicative of sleep apnea, using any of the above techniques.
13. Identify each probable event with an identity marker, or alternatively mark each event by its descending slope or by the slope ratio.
14. Treat the sleep apnea, either automatically, or manually, based on a diagnosis.
15. Repeat steps 1–14 to confirm the diagnosis and efficacy of treatment.

The above system represents the general concepts of one embodiment of the present invention. Other comparisons which incorporate the desaturation slope and the resaturation slope are also included within this teaching.

Figure 5:
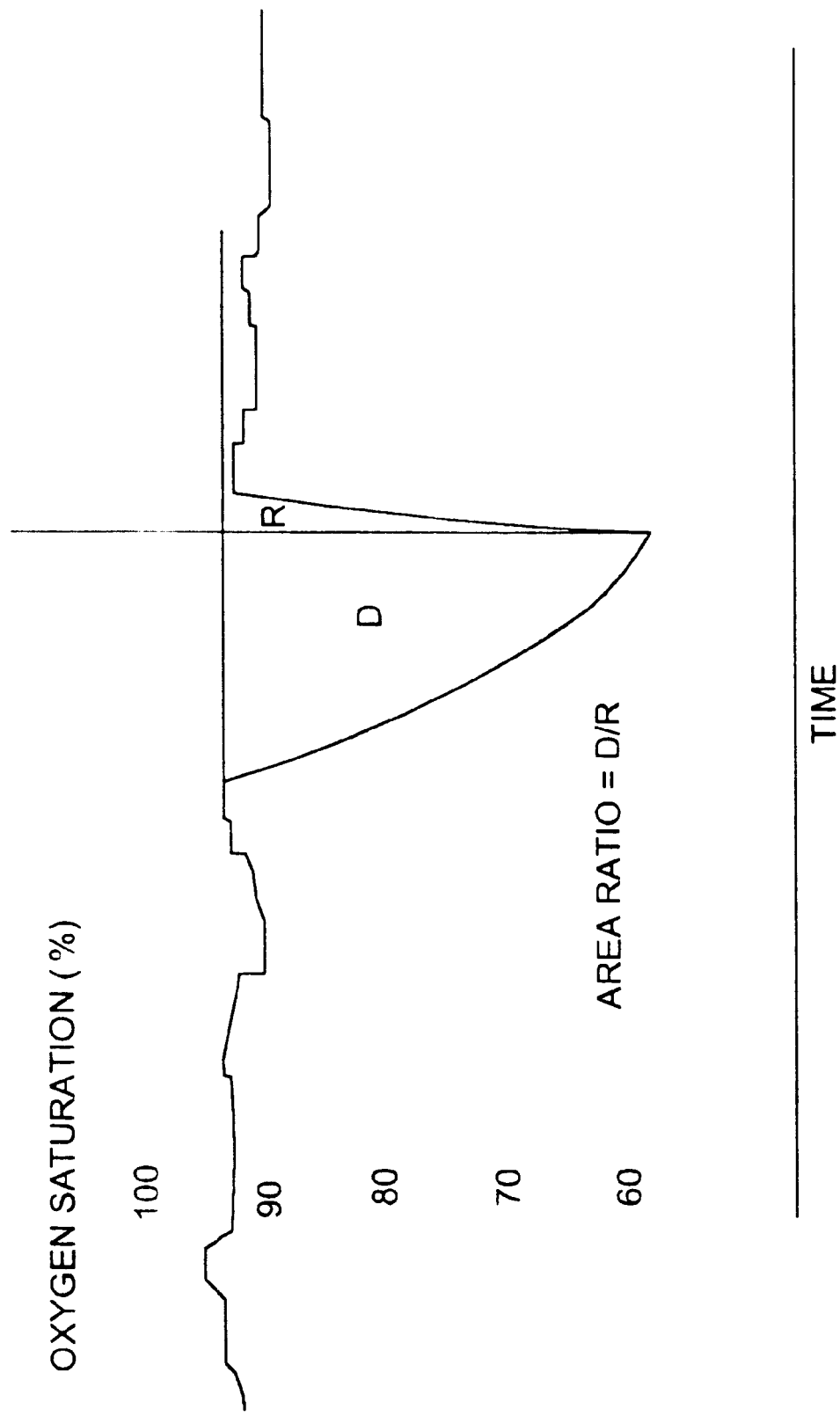
FIG. 5 shows a specific way in which a comparison can utilize the calculation of the area above each desaturation event compared to area above coupled resaturation event.

For example, FIG. 5 shows how a comparison can use the calculation of the area above each desaturation event compared to area above each coupled resaturation event. With this system, an x-axis is projected from a point of initial desaturation. A second y-axis is projected upward from the initial point of rise of saturation which signifies the onset of a resaturation event. The areas above the sloping lines, defined as D and R in the above figure, are then compared in a similar manner to that described in the previous embodiment.

In addition, the specificity and sensitivity of oximetry with respect to the diagnosis of sleep apnea is greatly enhanced by another embodiment of the invention which includes all of the multiple slope comparisons as described above. In such a system, in combination, the desaturation slope is compared to a desaturation slope which is consistent with a diagnosis of sleep apnea; second, the resaturation slope is compared with resaturation slopes known to be consistent with sleep apnea; third, desaturation slopes are compared with coupled resaturation slopes to define a slope index which is known to be consistent with sleep apnea; fourth, desaturation slopes and resaturation slopes are compared with other such slopes within the same record to identify slope similarity of the desaturation slopes and slope similarity of the resaturation slopes, respectively; furthermore, the similarity of the desaturation-resaturation slope index of the identified events can be compared; furthermore as previously discussed, consecutive slopes can be compared in relationship to the interval between desaturation events to determine whether a preceding desaturation event affects the slope of a closely after following desaturation event, and; finally, the mean of all desaturation slopes can be compared to the mean of all resaturation slopes to define an aggregate index.

In another preferred embodiment, the present invention identifies a phasic desaturation event to trigger storage or collection of at least one additional parameter of the patient. These additional parameters can be, for example, a recording of sound or video. When the microprocessor identifies specific coupled desaturation-resaturation parameters, which are physiologically consistent with sleep apnea, the microprocessor initiates the storage of selected data collected by at least one additional sensor.

Sound has been shown to be an important indicator of airway obstruction, however, many patients spend the majority of their night without major obstructive apneas. Therefore, if the entire night of sound were recorded, it would include a large amount of unnecessary sound recording, for only a small amount of useful data surrounding obstructive apneas. In the preferred embodiment shown in FIG. 1, the additional sensor includes a microphone 30 which can be integral with or carried by the probe 13 of the pulse oximeter 12 or which can be positioned in other regions near the patient during sleep. With this preferred embodiment, the microphone 30 is connected to an audio processor 32 of any known type, such as a Sound Blaster™ 16-bit processor. The sound is recorded digitally as a function of time. Alternatively, the sound may be Fast Fourier transformed ("FFT"), and the transform information may be stored. Alternatively, other means of sound or other recording can be utilized.

Preferably, the sound is continuously recorded throughout the night and most recent recording always maintained in short-term memory. If, after a finite period of time (for example, 4 minutes), no couples desaturation-resaturation event occurs which is specific for sleep apnea, the oldest part of the recorded sound will be erased or otherwise not marked for retrieval. If, however, a couples desaturation-resaturation event occurs which is consistent with sleep apnea, the identification of this event will trigger the marking and storage of the collected sound data during an interval preceding, during, and immediately after the event.

In the preferred embodiment, the total sound interval retained for each desaturation event includes the interval of the coupled desaturation-resaturation event, as well as one minute preceding and one minute following each such event; although this recording time can be further reduced for greater efficiency of memory utilization. In this way, the entire night will be monitored by oxygen saturation while sound is stored, but the information can be rejected to save memory unless a sleep apnea event is identified by pulse oximetry. If a sleep apnea event is identified, this will trigger the long-term storage of sound information surrounding that event. In this way, the efficiency sampling of sound that can be greatly enhanced since only small portions of sound need be collected in relationship to each apnea event.

Continuous recording of oxygen saturation and sound when indicated as a function of time can be digitally stored on any commercially available removable computer memory media, for example, a high-capacity floppy disc, or a removable Bernoulli disc, and then transported to a second microprocessor for evaluation by the physician and for printing. The entire record can be printed with a continuous graphical representation of oxygen saturation as a function of time. The sound can be graphically represented as a function of time by (for example, showing the volume as the width of the line and the frequency as its position along the y-axis). As discussed previously, such graphical representation of oxygen saturation can include specific markers indicating coupled desaturation and resaturation events which are physiologically consistent with sleep apnea.

Preferably, staccato or interrupted low frequency sounds may also be graphically represented preceding an oxygen desaturation event. Subsequently, variable high frequency sounds of low volume may be identified immediately preceding the recovery of oxygen saturation, indicating the presence of post-apnea hyperventilation. The physician can easily, therefore, determine whether these oxygen desaturation events are due to obstructive sleep apnea by identifying the sound parameters with which these couples desaturation-resaturation events are temporarily associated. Of course, all coupled desaturation events might not necessarily be associated with a typical sound pattern. However, throughout the night recording, patients with obstructive sleep apnea would be expected to have typical snoring sounds; whereas, patients with central sleep apnea from a periodic breathing or alterations in ventilation-perfusion mismatch would not be expected to demonstrate such sound parameters in relationship to such coupled desaturation-resaturation events.

The system is further advantageous in that it allows the physician to efficiently focus on portions of the night which are of the greatest interest. For example, the physician can specify a desaturation event identified by the microprocessor as an apnea, then either look graphically at the sound surrounding that event or, alternatively, listen to digitally recorded sound which surrounds a specific desaturation-resaturation event. It should also be clear that a video recorder could be activated in a similar manner, along with a sound recorder, to obtain critical bytes of a night's sleep for efficient evaluation. In this way, the diagnosis of airway obstruction can be confirmed, along with the diagnosis of sleep apnea, by utilizing a greatly simplified and less expensive system than conventional home polysomnography.

It is clear that, because of overlap with other disorders, the diagnosis of mild sleep apnea cannot be achieved by identifying a single coupled desaturation-resaturation event even when the event and all the associated slopes are physiologically consistent with sleep apnea. For this reason, the identification of a desaturation slope and a resaturation slope and a comparison of these slopes, even wherein all meet the criteria for sleep apnea, can only be said to identify an event that is physiologically consistent with apnea from the perspective of oxygen desaturation and resaturation waveform. It is the comparison of multiple desaturation events which is specific for sleep apnea as in the present invention.

Although, as per the previous embodiment, the analysis of slope parameters when multiple events are identified and counted is specific with respect to moderate to severe apnea, it is critical to achieve specificity for the large patient population that has only mild sleep apnea. Unfortunately, many disorders can produce oximetry waveform deflections which are repetitive and/or cyclical and of equivalent magnitude to those of mild sleep apnea.

Enhanced sensitivity must be achieved for patients with mild oximetry deflections due to sleep apnea. In addition to providing enhanced sensitivity it is important for a system to make a rapid diagnosis of the presence of instant sleep apnea for CPAP titration. The microprocessor must make a definitive and reliable assessment of the presence or absence of sleep apnea within a short interval to allow a higher number of upward CPAP titrations throughout the night to assure the minimum opening therapeutic pressure has been identified as will be discussed.

One preferred embodiment utilizes the continuous calculation and comparison of saturation slopes to identify sleep apnea to thereby enhance sensitivity for mild apnea and achieve rapid diagnosis of instant sleep apnea. In this embodiment, as is conventional, oxygen saturation is measured as a function of time and each saturation data point is stored as a function of the sampling frequency. The present invention then utilizes each new data point with a preset number of preceding data points (for example, four data points wherein the sampling frequency is 20/min. to derive a continuous instantaneous slope. The instantaneous slope is recorded as a function of time and can be plotted with saturation as a function of time on the same graph. In this preferred embodiment, the instantaneous slope is calculated as the slope of the line of best fit (as by conventional formulas) drawn through the specified number of saturation points, such as 3–5 data points. As each data point is added, the new slope is recorded as a function of this new data point with the first data point of the group deleted. This derives a continuous moving waveform of the calculated slope of oxygen saturation/second, which is shown graphically in FIG. 6. In the preferred embodiment, multiple consecutive slopes in the same direction are considered aggregate slopes and are averaged to produce a mean negative or positive aggregate slope. The continuous calculation and analysis of this slope waveform provides an enhanced specificity in the diagnosis of sleep apnea with minimal compromise in sensitivity since it is not dependent on a specific threshold deflection for the identification of apnea. Since sampling frequency will determine the configuration of any oximetry waveform. The greater the sampling frequency, the more reliable will be the slopes in the presence of very mild sleep apnea. For mild sleep apnea, a sample recording interval of 3 seconds (wherein the lowest recorded saturation with this interval is recorded) is adequate, although a continuous sampling for each pulse is optimal for this diagnostic system. In sleep apnea, oxygen desaturations generally occur within clusters. For this purpose of the present invention, a cluster is said to be present when at least three consecutive negative slopes interrupted by positive slopes have occurred wherein the intervening interval between each consecutive negative slope is less than two minutes. The present inventor has discovered that the presence of a cluster of at least three negative slopes meeting these criteria and wherein the consecutive negative slopes are similar (for example, falling within a range of the initial slope ±60%) and wherein the negative-positive slope ratios are within 3.5–10.5 is clearly diagnostic of a sleep apnea cluster and can be said to comprise a sleep apnea slope cluster complex, referred to hereinafter as a "slope cluster complex." Such a slope cluster complex 50 is graphically shown in FIG. 6.

In the presently preferred embodiment, the identification of slope cluster complexes is used to facilitate CPAP titration. With this system, the microprocessor can initiate nasal positive pressure at, for example, a pressure of 4 cm of $H_2O$ upon identification of a slope complex. As is known in the art, this pressure can be incremented from an initial 0 pressure up to 4 cm of $H_2O$ pressure over a period of two to five minutes or longer to minimize the potential for arousal with initiation of therapy. Throughout this time, the pulse oximetry waveform is monitored for any evidence of further slope cluster complexes. If an additional slope cluster complex occurs after the CPAP has reached 4 cm of pressure, the microprocessor again in increases the CPAP level by an additional 1 cm during the final negative slope of this new complex. If an additional after-following slope cluster complex again occurs the microprocessor again increments, the nasal CPAP pressure by an additional 1 cm during the final negative slope of this complex. The microprocessor will continue to monitor for further complexes and similarly, increment the nasal CPAP by 1 cm upon each recurrence up to a present pressure limit of, for example, 15 cm. When no further such complexes occur subsequent to an increment in CPAP, this level is maintained for a sustained period, which should preferably be equal to or exceed 15 minutes. If any further slope cluster complexes occur within this interval, the microprocessor will increment CPAP by 1 cm of $H_2O$ pressure and this pressure will be maintained until no further complexes are identified for 15 minutes. Once the baseline oxygen saturation has been without further slope cluster complexes for 15 minutes, the CPAP is eliminated by the microprocessor. This can occur slowly over a period of, for example 2 minutes, to minimize the potential for arousal to be induced by sudden reduction of nasal CPAP. The patient is then monitored again for evidence of recurrent slope cluster complexes, as previously described. If a slope cluster complex is again identified, the CPAP is incremented in a similar fashion to that previously described; however, to allow more rapid titration, the starting level of CPAP is set at a minimum of 2 cm H2O below the final therapeutic level, which level was achieved during the preceding titration. For example, if the preceding titration achieved a therapeutic CPAP of 10, the starting titration level for the titration would not be less than 8. (However, the CPAP unit can be ramped slowly up to 8 over a period of 30 seconds, rather than suddenly initiating this pressure.) Again, incremental CPAP titration is utilized for each consecutive slope cluster complex, as for the initial titration, until no further slope complexes occur for the specified time interval of 15 minutes. After the interval of 15 minutes without a slope cluster complex has concluded, the CPAP will again be withdrawn, as previously described. The patient will be monitored and, if another slope cluster complex occurs, a new titration will be initiated. In this way, as many as 12 or more separate complete CPAP titrations can occur throughout the night. Actually, however, less CPAP titrations generally will occur in a majority of patients since often there are no more than 4–5 separate clusters of desaturation events in any single night. To increase the number of titrations, CPAP may be withdrawn after a shorter specified interval of absent slope cluster complexes, such as five minutes or upward titration may be more rapid, for example with each consecutive negative slope within a slope cluster complex after an initial 3 negative slopes have occurred. In this way, three or four CPAP titrations may occur within a single 30 minute desaturation cluster.

The comparison of consecutive slopes within a cluster allows increased specificity with less loss of sensitivity by accepting the diagnosis of sleep apnea without requiring a specific magnitude of desaturation from the baseline. This is particularly true when the slope cluster complexes are obliterated by initiation or incrementation of the CPAP levels. There is, of course, a time delay between the development of apnea and the onset of oxygen desaturation identified by the pulse oximeter. Due to this delay, it is not generally possible to arrest a specific negative slope by the initiation or upward titration of nasal CPAP during said negative slope unless the initiation occurs within a very short interval after the negative slope has started. Even when initiated early, substantial desaturation will continue, even if complete elimination of the obstruction immediately occurs upon initiation. The initiation of nasal CPAP during a slope cluster complex, therefore, may effectively treat and prevent the next negative slope, but unless the slope is quite prolonged the initiation or upward titration of CPAP may not interrupt the negative slope which is already in progress since, indeed, the physiological mechanisms causing the negative slope may have already have been completed. Anticipating this delay (which may be 20 seconds or more) the CPAP can be initiated or titrated upward immediately upon identification of the third negative slope or at the end of the second negative slope. Arrest of the third negative slope after the expected delay can provide diagnostic value.

The purpose of this repetitive cyclic titration is to identify a breakpoint range of CPAP which provides adequate pressure to break a cycle of desaturations by preventing further apnea episodes. The effect is diagnostic and further identifies the level of CPAP required for long-term therapy. The presence of even very small desaturations which occur with slope cluster complexes and which are consistently eliminated by a finite range of nasal CPAP pressures, is clearly diagnostic of sleep apnea and specifies the level of CPAP that is required for effective therapy. The recording of continuous CPAP pressure (as is known in the art), may be simultaneously performed and, the recurrent titration of the breakpoint can be identified by plotting the slope waveform simultaneously With CPAP to verify that actual breakpoints are occurring as a function of CPAP titration, rather than by chance. It is clear that with any single episode of titration, spontaneous cessation of steep apnea cycles may occur at any time during the titration, providing an initial "breakpoint" which may actually not be truly a function of adequate therapy. However, the consisten identification of a single breakpoint range (for example, 8–10 cm) at which point, for example, four separate slope cluster complexes were terminated and wherein no further slope cluster complexes occurred when this level was maintained would clearly identify adequate therapy and would identify the lowest adequate therapeutic pressure.

Ideally, the entire titration process occurs over two nights. The initial titration process involves recurrent initiation and withdrawal of nasal CPAP, as previously described, over cycles of 15–30 minutes throughout the night. The microprocessor identifies the breakpoint pressure which is adequate to break all slope cluster complexes throughout the entire night's study. This pressure level is designated "the therapeutic breakpoint CPAP" level and is recorded and stored for the second night's study without requiring a second home visit or modem control for adjustment of the CPAP. Upon initiation of the second night's study the microprocessor automatically ramps the CPAP unit to the therapeutic breakpoint CPAP value over a specified interval of, for example 5–30 minutes. The patient is then maintained on this pressure level throughout the night to assure the pressure is adequate.

Figure 6:
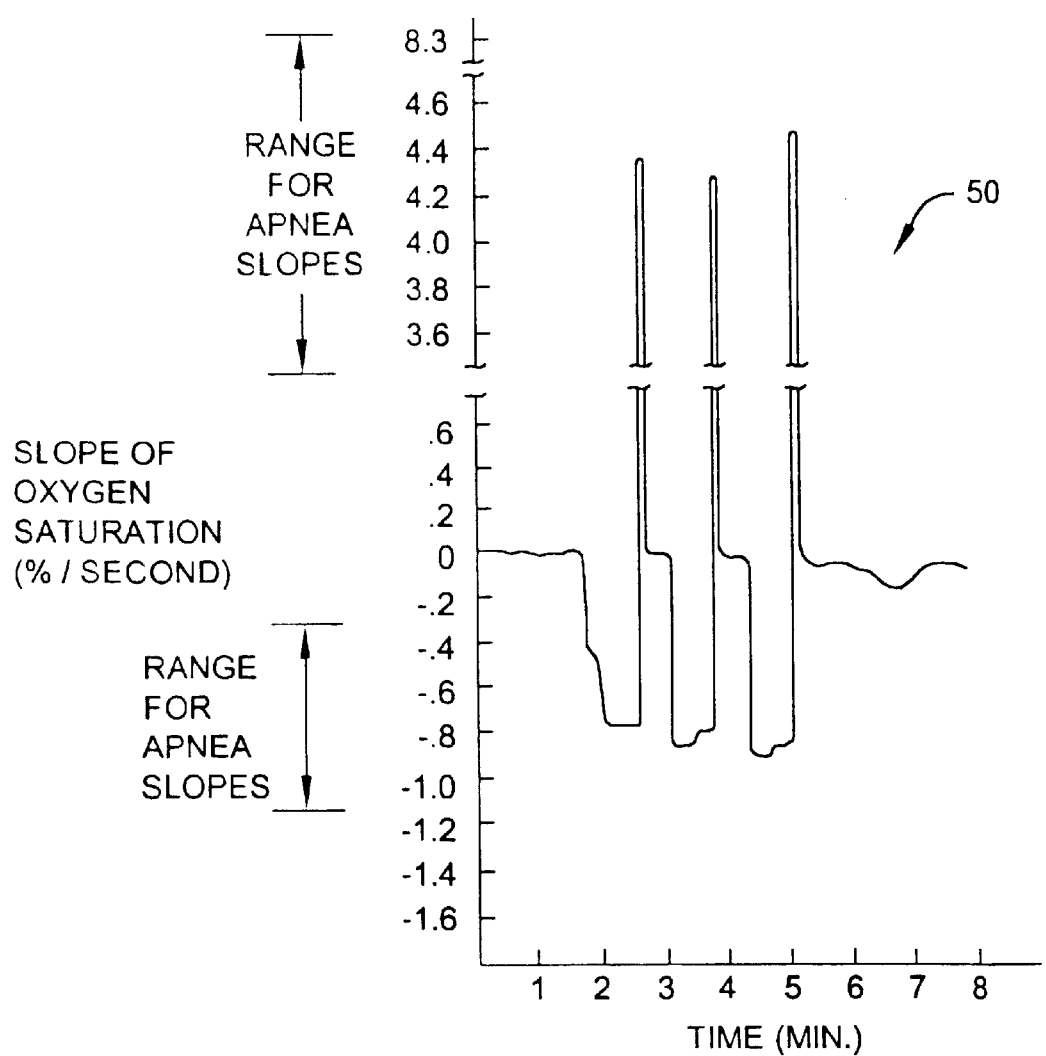
FIG. 6 shows a slope cluster complex plotted as slope against time.

Importantly, for the sleep apnea diagnostic system to be utilized in clinical medicine, a hard copy must be produced so that the physician can overread the interpretation of the computer because many cardiac and pulmonary disorders, as well as artifact, can produce deflections with similar magnitude and configuration with that of mild sleep apnea. It is well known that differentiation of mild sleep apnea by visualizing the patterns of conventional oximetry waveform plots of oxygen saturation versus time is non-specific. The present invention describes a system which derives and analyzes continuously the multiple slope patterns to make a definitive diagnosis of sleep apnea quickly, however, for this to be accepted by the medical community, the physician must have a new way to interpret the oximetry tracing waveform and thereby overread the interpretation of the computer. The present inventor has discovered that the slope cluster complexes are easily visualized even in the presence of only mild apnea by graphically representing the continuous, instantaneous slope of oxygen saturation [as $\Delta$ Saturation (%)/$\Delta$ Time (seconds)] as a function of time, where slope is placed on the y-axis and time is placed on the x-axis. Utilizing this representation, the effect of the limited magnitude of the deflection is greatly minimized, and the effect of the particular slope characteristics are maximized graphically and visually. The effect of visually and graphically representing continuous slope as a function of time is shown in FIG. 6. This graphical representation allows the physician to overread the interpretation of the computer by identifying visually the presence of slope cluster complexes. As noted, this graph demonstrates the slope of the oxygen saturation as a function of time where:

slope=change in saturation $\Delta$ S (%) /$\Delta$ T (seconds), and where time is in minutes.

The y-axis includes marked regions which identify slopes that are physiologically consistent with sleep apnea. For example, with respect to negative stores, the physiologically consistent region is marked as –0.3 to –1.1 and with respect to positive slopes, the physiologically consistent region is marked as 2.5 to 8.3. As oxygen saturation data points are measured and stored, continuous slope calculations are made. Alternatively, consecutive negative slopes may be defined as a single aggregate positive or negative slope and may be average for the purposes of graphical representation and interpretation.

The previously-described apparatus is both a diagnostic tool for sleep apnea and a fix therapeutic pressure identifier. Specifically, it identifies the minimum fixed therapeutic pressure than can reliably prevent substantially all future apnea episodes in a given patient. This pressure is printed and identified as the minimum therapeutic break pressure or optimal nasal CPAP pressure. In the preferred embodiment, the microprocessor may set the nasal CPAP pressure on the nasal CPAP unit for long term therapy so that this pressure is subsequently maintained for this patient without further adjustment by patient, physician, or home health personnel. This therapeutic pressure which had been previously identified is, therefore, fixed and will be utilized, for example over the next 6–12 months, until a repeat study is performed at this pressure to confirm that further apneas have not redeveloped or that a lower pressure therapeutic (such as after loss).

While this language herein refers to oxygen saturation, it should be understood that gas exchange parameters could be determined in ways other than those specifically disclosed herein, but are included within the scope of this teaching. For example, sequential and cyclic time-dependent storage of carbon dioxide in body compartments during sleep apnea can be similarly used to diagnose sleep apnea using, for example, the comparison of consecutive slopes of maximum exhaled $pCO_2$. Also, inspiration-triggered variable pressures, such as BIPAP, may also be titrated in a similar manner to that described herein for CPIAP.

As previously described, obstructive sleep apnea produces a unique pattern of oscillation of oxygen saturation which generally occurs within clusters. The physiology of factors inducing upper airway instability is pivotal toward the derivation of the clusters which are identified on the timed oxygen saturation wave form. Since sleep apnea itself can be considered a normal event, it is less important to identify the presence of an episode of sleep apnea than to identify the presence of upper airway instability. In the presence of upper airway instability clusters of coupled desaturation-resaturation events will occur. The presence of such clusters meeting specific criteria is more than diagnostic of sleep apnea. It is diagnostic of a severity of upper airway instability sufficient to produce an oscillatory aberration in the normally homeostatic and stable interaction between respiratory drive, upper airway tone, the arterial oxygen saturation.

Table 1 illustrates the variable Oscillatory Respiratory Drive during sleep in the presence of superimposed upper airway instability (Note: Airway closure (Apnea) produces a block between a progressive increase in respiratory drive and its normal effect to increase arterial oxygenation. From the perspective of respiratory drive oscillation during sleep, each apnea functions like a potential energy store which is precipitously released upon the termination of the apnea. The stored energy for increased drive is a direct function of the magnitude of oxygen desaturated hemoglobin. When this energy is precipitously released, it function as a sudden new force impacting the oscillating system thereby preventing extinguishment. This repetitive force loading thereby induces pronounced and sustained oscillations which are manifested by the oximetry wave form as a cluster of coupled desaturation-resaturation events. For this reason a sustained cluster, (wherein the precipitous release in transmission of heightened respiratory drive is manifested by a rapid increased in oxygen saturation after each fall) is diagnostic of sleep apnea and more important diagnostic of upper airway instability during sleep (i.e. obstructive sleep apnea).

Therefore, in the presence of sufficient upper airway instability, from the perspective of gas exchange, and in particular as measured by the arterial pulse oximeter, the oscillatory sequence is substantially always a cluster.

The above system may be modified in the presence of very severe upper airway instability. In this condition hypoventilation may not be a necessary antecedent to apnea and indeed upper airway patency may become completely arousal dependent in certain sleep stages (e.g. during REM) or with a particular body or head position. In this highly unstable system the oscillatory frequency is a function of the arousal threshold (which determines the length of the apnea) and the duration of each arousal (which determines the time interval between recovery and the next desaturation). These are variable as a function, for example of sleep stage, and the magnitude of sleep deprivation. For this reason, in the presence of a potentially highly unstable airway the intracluster desaturation/resaturation frequency may be variable. Since, in the absence of arousal, the highly unstable airway will promptly occlude, rather than being driven by more complex oscillation of respiratory drive as defined above, such a highly unstable system is defined by a more simple on and off alternation of airway patency (as a function of the presence or absence of the arousal state). In the presence of a highly unstable upper airway, the oximetry wave form will appear as if a oxygen flow switch was turned off for a specific time interval to a system having a relatively finite oxygen runoff and then turned back on precipitously releasing a high rate of flow rate of oxygen back into the system only to again be promptly turned off again. Although the nadir of this wave form may appear similar to that associated with a less unstable upper airway, the inter-event peaks often present a sharper angle reflecting the substantially absolute "on or off" mechanism of gas flow to the patient especially if each arousal is brief.

Since the variations in arterial oxygenation which comprise a cluster are derived from an oscillating respiratory drive system, within each cluster, the desaturation/resaturation events occur at relatively regular intervals as a function of the temporal relationship between overshoot ventilation, hypoventilation, and upper airway collapse or as a function of the existence of a threshold range of oxygen desaturation which will "turn on" arousal. Within a cluster, each desaturation/resaturation event has a similar shape. In some cases, the desaturation/resaturation events within a given cluster start out with fairly small desaturation magnitude (change from baseline), increase in absolute magnitude and then decrease in magnitude before end of the cluster. In other words, the magnitude of the desaturation/resaturation events waxes and wanes once during a cluster. The clusters, themselves, typically do not occur at regular intervals and the clusters also do not have the same time length. The signal interval between clusters generally has no particular interesting characteristics and might be thought of as being a signal with some noise and/or artifact. Patients who do not have OSA, on the other hand, may have desaturation/resaturation events but they do not have the same periodicity that is apparent with OSA patients and these desaturation/resaturation events often do not have any particular characteristic shape.

There are several methods for transforming a time domain signal, i.e. a signal which varies in amplitude as a function of time, into the frequency domain to determine its frequency content. Fast Fourier transform (FFT) analysis, a well-understood and well-utilized analysis tool, is one such method. Many efficient hardware and software algorithms have been developed and implemented which can perform FFT analysis on a time-domain signal segment. An FFT algorithm approximates a time domain signal segment with a series of sinusoidal functions. Each function in the series has a certain amplitude, frequency and phase. If these functions are summed in the series point-for-point over time, the resultant time-varying signal will resemble the original time domain signal segment analyzed. The more sinusoidal functions used to approximate the signal, the better the resemblance. The time domain signal is represented in the frequency domain by plotting the amplitude versus frequency of the sinusoids in the series. This gives a visualization of the frequency content or frequency spectrum of the original signal. It allows for visually identifying the dominant frequencies that make up the original time domain signal. Another common visualization of the original time-domain signal segment is the power spectrum which is constructed by plotting the square of the amplitudes of the sinusoids resulting from FFT analysis versus the frequency of the sinusoids in the series.

Frequency domain analysis of the $SpO_2$ signal, as performed with an FFT algorithm, reveals several qualitative and quantitative characteristics which provide a unique signature for OSA. In the frequency domain, signals recorded from OSA patients will have at least one and at times two specific dominant (high amplitude) frequency intervals in the frequency spectrum, depending on the particular characteristics of the signal and time length of the signal segment analyzed. The primary frequency interval will result from the individual desaturation/resaturation events. This interval will have a fairly sharp peak because the events are somewhat sinusoidal in shape and are fairly equally spaced in time. Only a few frequency components will be needed to reconstruct this part of the signal. The frequency of the peak power (FP) will range between approximately 0.01 Hz to 0.08 Hz. The second dominant frequency interval will result from the fact that the desaturation/resaturation events often occur in clusters. If the signal segment being analyzed includes several clusters, the result will reveal a second dominant frequency interval which will correspond to the periodicity of the clusters in time. It has been shown that the desaturation and resaturation slopes along with the time between desaturation/resaturation events, in the time domain, fall within a narrow range for OSA patients. Therefore, the inter-patient variability of the first described dominant frequency will be relatively small. It has been found that when definable clusters appear in the $SpO_2$ signal of OSA patients, the clusters do not often occur at regular intervals and are not of the same time length. At times the entire nights tracing is comprised of a single continuous cluster. Therefore, the second described frequency interval, if observed, will display a large inter-patient variability. Signal intervals between clusters will generally have a flat spectrum because these signal intervals are composed mainly of broad-banded noise and random artifact or defections derived from physiologic mechanism which are not inherently oscillatory. The majority of $SpO_2$ signals from patients who do not have OSA have no particular outstanding features but appear rather as random noise, non periodic deflections and/or artifact, the frequency spectrum of these signals will generally be broadbanded, flat, and may lack any dominant high-amplitude frequency intervals.

Figure 7:
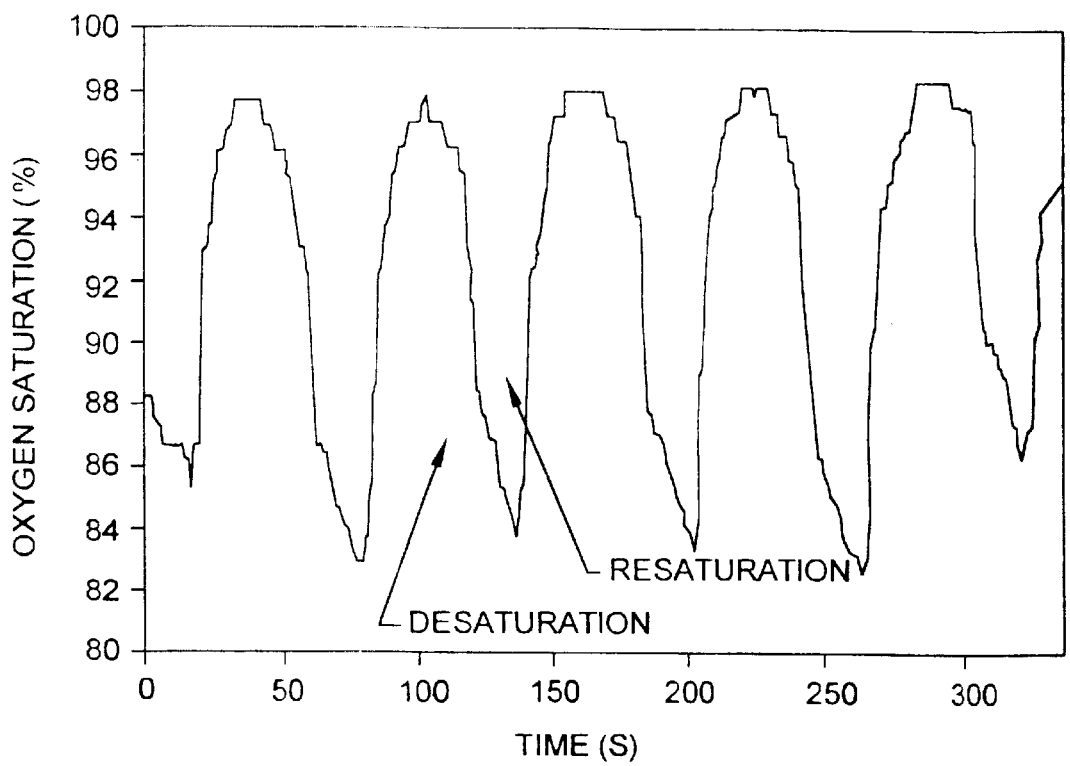
FIG. 7 shows a slope cluster complex plotted as oxygen saturation against time.
Figure 8:
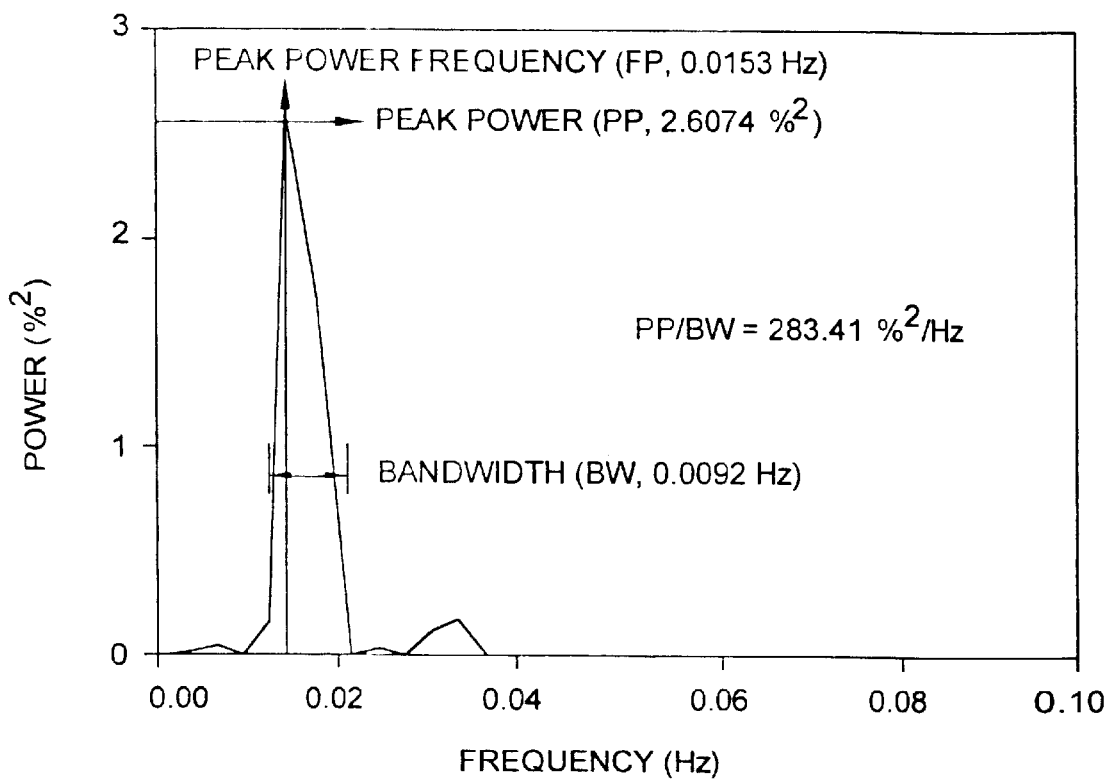
FIG. 8 shows the power spectrum of the signal segment of FIG. 7.
Figure 9:
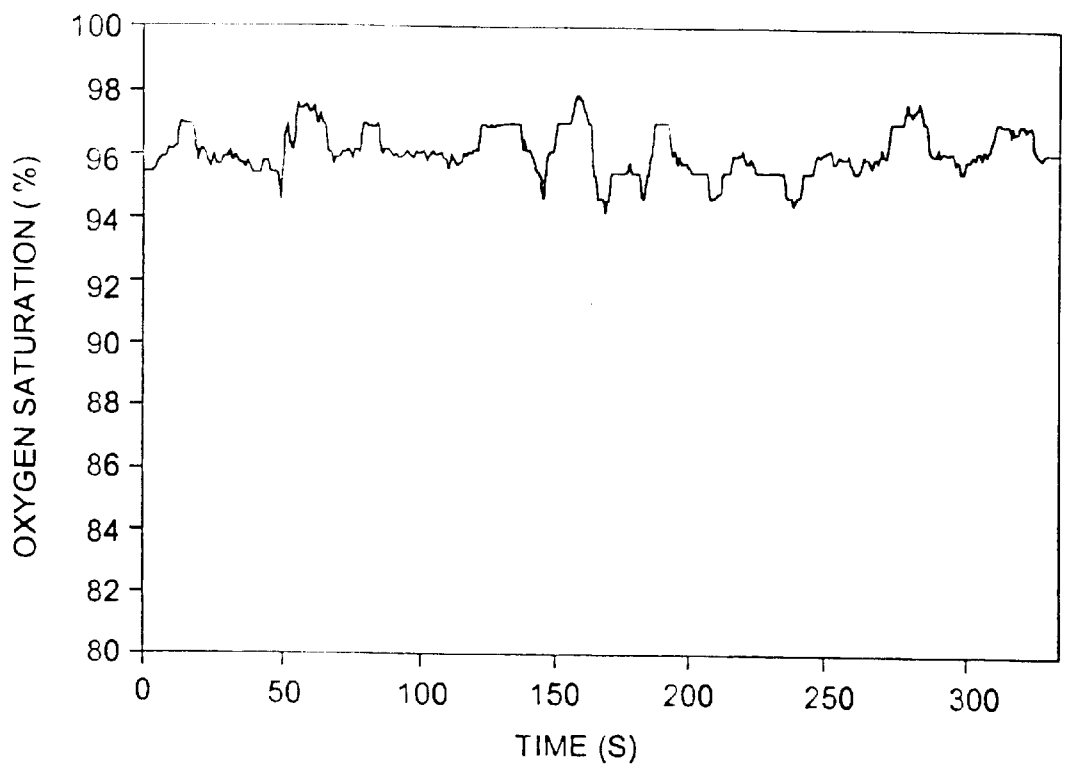
FIG. 9 shows a time domain signal segment from an OSA disease free patient with a noisy baseline.
Figure 10:
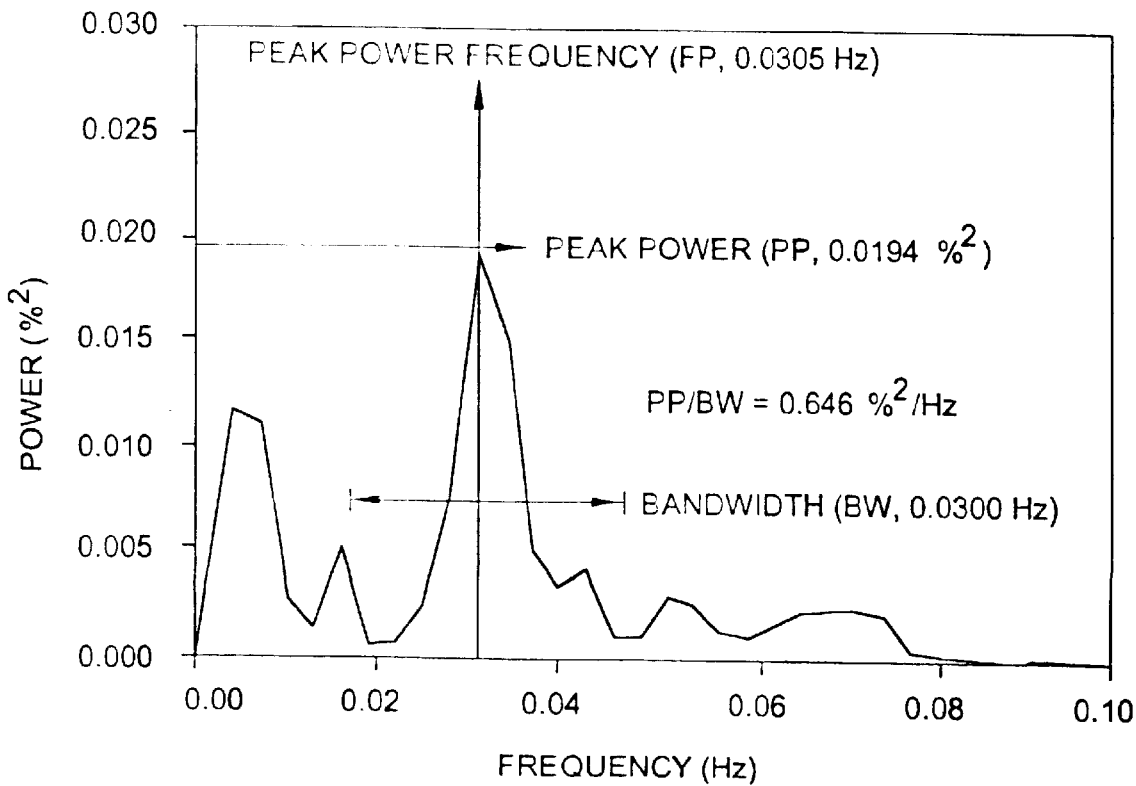
FIG. 10 shows the power spectrum of the signal segment of FIG. 9.

There are several quantitative parameters that can be extracted from the power spectrum of the SpO2 signal that provide a signature for OSA. Of particular note is the ratio peak power (PP)/bandwidth (BW). Peak power is defined, for a given time-domain signal segment, as the highest power in the power spectrum. The BW, of the same signal segment, is defined as the difference between the highest frequency below which resides a given percentage of the total power minus the lowest frequency above which resides the same percentage of total power. FIGS. 7–10 demonstrate the utility of this ratio in identifying OSA. FIG. 7 shows a segment of the time-domain SpO2 signal recorded from a patient with OSA and illustrates the characteristic repetitive oxygen desaturation/resaturation events seen with this disease. FIG. 8 shows the power spectrum of this signal segment, which resulted from FFT analysis following appropriate filtering and windowing. Because the time-domain signal is somewhat sinusoidal in shape and periodic with near constant period, the power spectrum shows a narrow frequency interval around the PP which is located in the spectrum at the frequency (FP) of the desaturation/resaturation repetition rate. The narrow BW enhances the high PP to yield a large PP/BW ratio value. In contrast, FIG. 9 shows a time-domain signal segment from an OSA disease-free patient. In this patient, the saturation tends to rise and fall during the segment but show less periodicity and more noise. The resulting power spectrim (FIG. 10) shows a broadband signal with peaks that have much less power than in FIG. 8. As a result, the PPIBW ratio is several orders of magnitude smaller than in the OSA patient.

Another important frequency parameter which can be used, in combination with other parameters, to identify patients with OSA is the peak power frequency (FP), defined as the frequency containing the peak power, PP. It has been shown that the rate at which desaturation/resaturation events occur falls within a specific range and is mostly independent of a patient's physiology and habitus Therefore, the FP for OSA patients fall within a definable range of frequencies. This range is approximately 0.01 Hz to 0.08 Hz.

The value of the PP/BW ratio and FP as diagnostic parameters for OSA is illustrated in FIG. 11. The median (±25 percentile) of PP/BW, in the range 0.01 Hz to 0.08 Hz, is plotted for both disease-free and OSA patients. The PP/BW is significantly greater for the OSA patients than for the disease-free patients. This occurs because the PP is higher and the associated BW is narrower for the OSA patients than for the disease-free patients. FIG. 11a illustrates another use of the PP/BW ratio for diagnosing. This data was generated in a similar manner as in FIG. 11 except that the total of all PP/BW values over the sleep session for each patient, rather than the average, was used as the diagnostic parameter. All other aspects of the analysis were the same as in FIG. 11. This summation parameter represents the area under the PP/BW vs. time curve over the sleep session. As in FIG. 11, the median (±25 percentile) of the PP/BW summation values was plotted for both disease and OSA patients. The PP/BW summation is significantly greater for the OSA patients than for the disease-free patients. In this patient sample, the PP/BW summation achieved an 89% sensitivity with an 82% specificity as a diagnostic parameter for OSA, when the threshold for diagnosis was set at 175%% Hz.

Since OSA patients often experience multiple clusters of desaturation/resaturation events during a sleep session, the PP and PP/BW during these clusters is virtually always larger than during periods of normal, non-apneic sleep. For this reason, a patient may be diagnosed as having OSA if, for instance, either PP or PP/BW or both PP and PP/BW exceed a specific threshold—for example, PP>5%%/Hz and/or PP/BW>175%%/Hz—a specific number of times during a sleep session or for a specific cumulative duration (e.g. 3 times or for a total cumulative duration of 15 minutes. These thresholds would be exceeded during a time interval when the patient is experiencing a cluster of desaturation/resaturation events.

Figure 12:
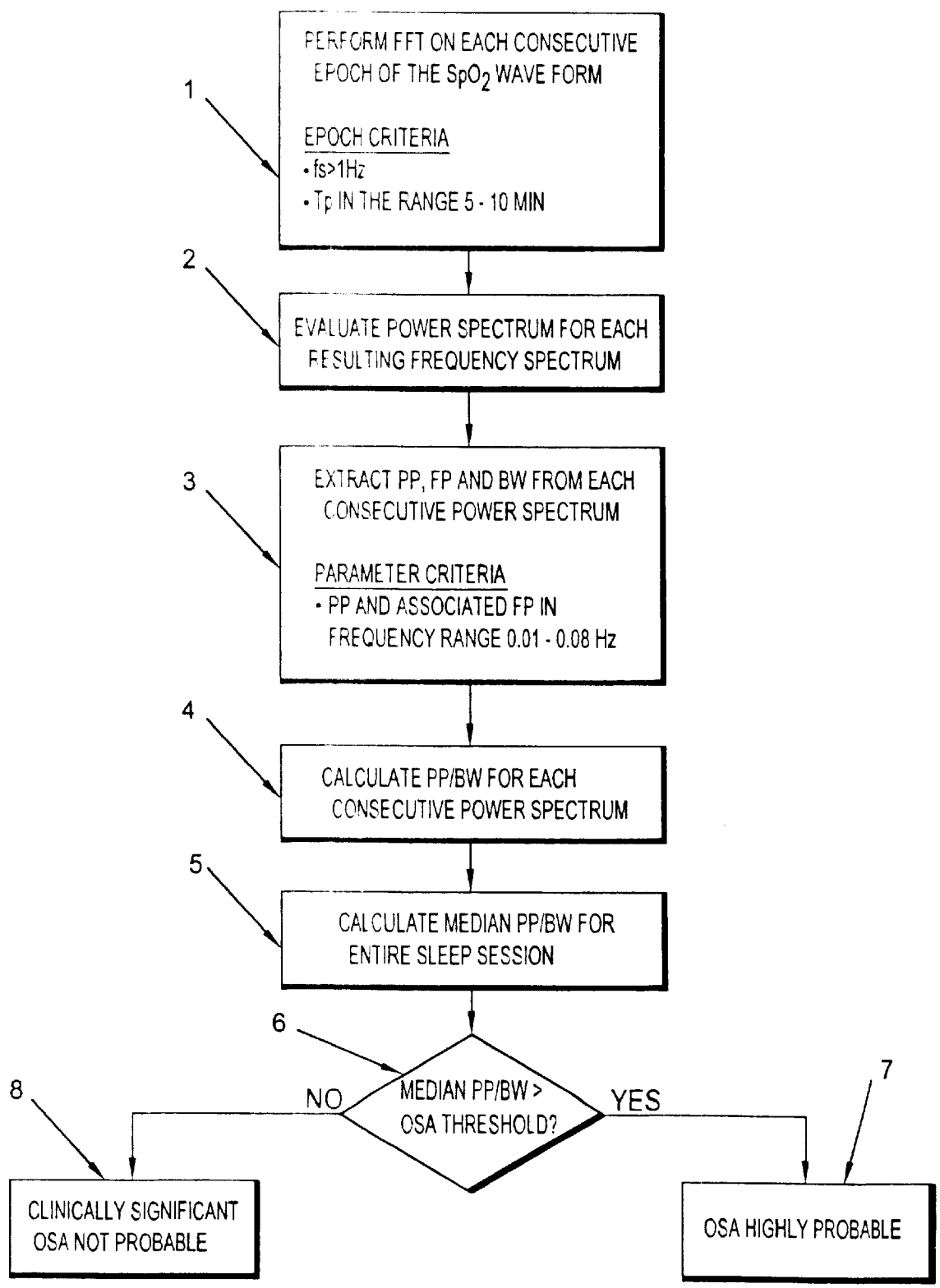
FIG. 12 shows one preferred frequency domain algorithm for screening patients with obstructive sleep apnea.

A block diagram for one presently preferred embodiment for screening for patients with OSA utilizing a frequency-domain algorithm to achieve a high sensitivity is shown in FIG. 12. The consecutive epochs of the nocturnal $SpO_2$ wave form are transformed into the frequency domain via FFT analysis 1. The time-length of each epoch tp is identical and in the range 5–10 min. The sampling frequency fs of the wave form is >1 Hz. The power spectrum of each resulting frequency spectrum is then evaluated by squaring the amplitude of each component of each frequency spectrum 2. The peak power PP and peak power frequency FP, in the frequency range 0.01–0.08 Hz, and the power spectrum bandwidth BW are then extracted from each power spectrum 3. The peak power/bandwidth ratio PP/BW is then evaluated for each power spectrum 4 and the median PP/BW is calculated for the entire sleep session 5. This median PP/BW is compared with the OSA threshold PP/BW 6 and if it is greater than the threshold then probability that OSA is present is considered very high 7 (positive screening test). Otherwise, clinically significant OSA is virtually ruled out 8.

Figure 13:
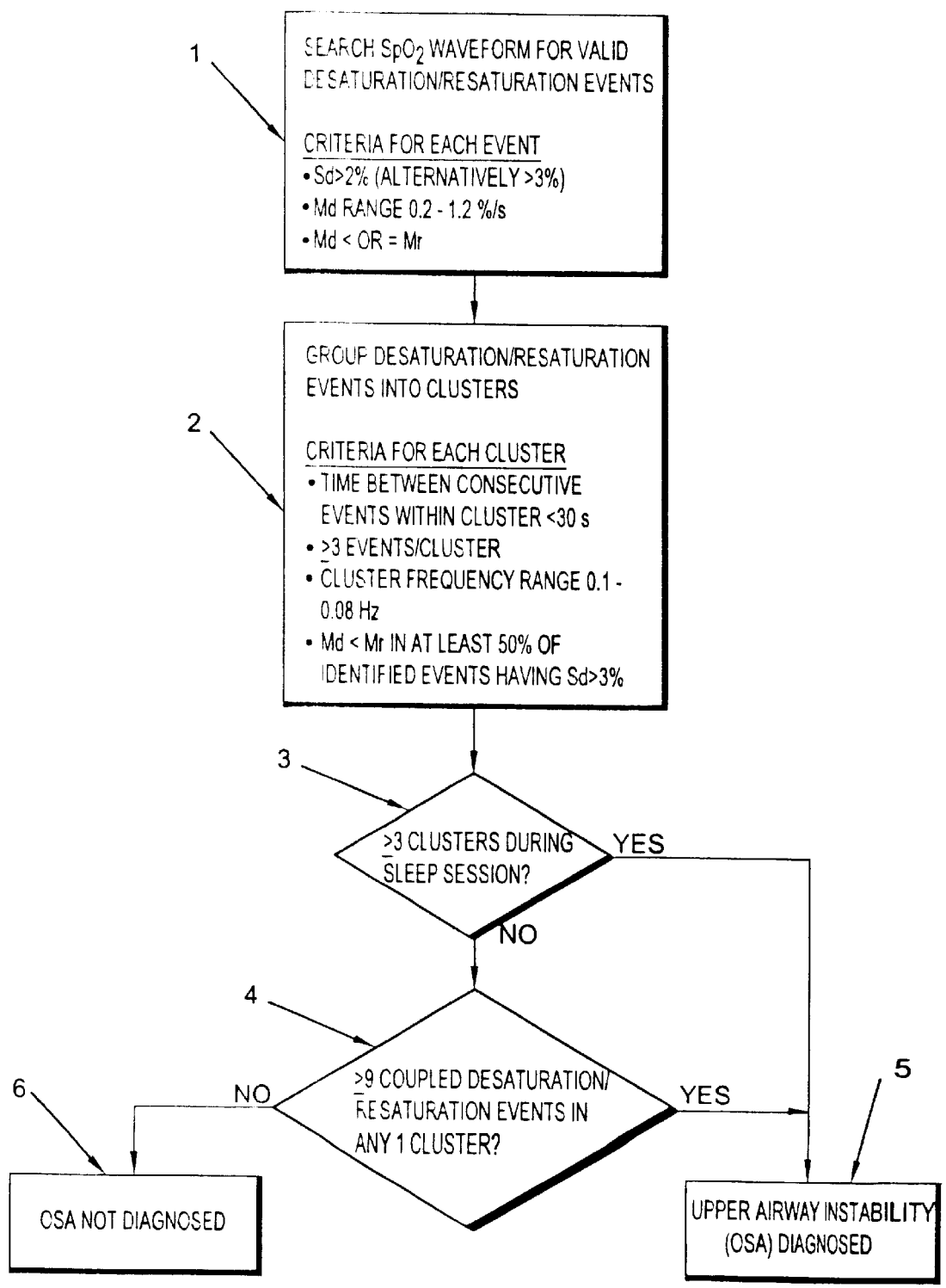
FIG. 13 shows one preferred combined time and frequency domain algorithm for diagnosing patients with obstructive sleep apnea.

A block diagram for the presently preferred embodiment for diagnosing patients with OSA is shown in FIG. 13. This embodiment incorporates a combined time and frequency-domain algorithm to achieve both high sensitivity and specificity for clinically significant OSA. The combined time-frequency algorithm has the advantage of providing differentiation between other sleep disordered breathing disorders associated with enhanced respiratory drive oscillations (e.g. Cheyne-Stokes Respiration) which may exhibit frequency parameters which are similar to obstructive sleep apnea and therefore less subject to differentiation when a frequency algorithm is applied in isolation. The nocturnal $SpO_2$ wave form is first searched to identify all desaturation-resaturation events 1. A valid desaturation/resaturation event is defined as consisting of a desaturation Sd of >=2% (>=3% can be used also) from baseline with a desaturation rate Md in the range 0.2–1.2%/s. This is followed by a resaturation back to baseline with a resaturation rate Mr slch that Md<=Mr. Because a desaturation/resaturation event has a characteristic shape, a range of spatial image templates can be constructed and cross-correlated along the wave form in order to find sections of the wave form which are highly correlated with the template either to locate a desaturation/resaturation event or to identify the cluster pattern. All of the desaturation/resaturation events are then grouped into clusters 2. A cluster is defined as a group of at least three coupled desaturation/resaturation events where the time between each consecutive coupled event is <30 s, the dominant event frequency falls in the range 0.01–0.08 Hz, Md<Mr when Sd>=4%. Then, OSA is diagnosed 5 if at least three clusters occurred during the sleep session 3 or if at least one clustered had at least nine coupled desaturation/resaturation events 4. Otherwise, clinically significant OSA is virtually ruled out 6.

Although the presently preferred embodiments of this invention have been described, it will be obvious to those skilled in the art that various changes and modifications may be made without departing from the invention. Therefore the claims are intended to include all such changes and modifications which may be made therein without departing from the invention. Therefore the claims are intended to include all such changes and modifications that fall within the true spirit and scope of the invention.

In conjunction with that previously discussed, the present inventor has discovered an apparatus and method of waveform analysis for the diagnosis of sleep apnea which can be used to evaluate a range of waveform including oximetry and exhaled carbon dioxide. For reasons noted supra, with respect to the diagnosis of sleep apnea, the oximetry waveform (with or without combination with digital sound) is preferred. The presently preferred embodiment includes a computer program for recognizing the basic cluster pattern (which pattern has been previously described) through the use of object designation to identify each component of the pattern and then though pattern reconstruction within the program. The present inventor has discovered that the identification of this pattern, even in isolation, wherein sequential oscillations are sufficiently perpetuated to produce recognizable clusters is indicative of significant sleep apnea since the recognizable cluster is in fact a sentinel event which indicates the presence of much more frequent, less severe events which do not result in sufficient desaturation for recognition. Specificity is derived by requiring a specific pattern or sequence of events meeting predetermined criteria or characteristics within this sentinel cluster, which pattern or events are the product of a combination of ventilation control instability and upper airway instability. Whereas, sensitivity is derived by eliminating the requirements of a certain number of events per hour such that the recognition of a specific sentinel cluster pattern is sufficient to make the diagnosis. One presently preferred method includes the identification of specific waveform objects and the comparison of the characteristics (for example the slope) of these objects in a manner similar to that previously discussed. The waveform is segmented into a specific sequential basic object (the saturation Dipole) having the characteristics of polarity, duration, and slope and from which all additional objects are derived. The system includes a microprocessor which divides the basic timed oxygen saturation waveform into said slope defined dipoles and then further classifies sequential components of the waveform as slope and interval derived basic objects for microprocessor analysis. The microprocessor then performs an analysis of the objects to further derive more complex objects of the oxygen saturation wave form called bipolar oscillations and slope clusters (which comprise multiple bipolar oscillations). These complex objects are built by the microprocessor by first identifying the basic object and then by adding each new sequential basic object to the preceding objects when said identification indicates that an appropriate basic object has occurred within an acceptable order and within an acceptable time interval. The building of complex objects from the repetitive derivation of basic objects along a timed waveform exploits the unique self perpetuating physiological events which occur during obstructive sleep apnea and which produces clustering of similar oxygen saturation slopes and intervals within predictable intervals of each other and in a predictable order sequence.

One embodiment of the system is configured and operates as follows:

1. A microprocessor based sleep apnea diagnostic system being constructed to:
2. Measure oxygen saturation.
3. Store oxygen saturation as a function of time to derive a saturation to time waveform.
4. Identification of two consecutive data points along said waveform said data points comprising, for the purpose of microprocessor analysis, a basic object specified as a saturation dipole or "Dipole" and then to;

Define the Dipole as positive when the second data point is higher then the first point.

Define the Dipole as negative when the second data point is lower then the first point.

Define the Dipole as neutral when the second data point is the same as the first point.

(A threshold magnitude of increase or decrease may be used to define when the second data point is specified as higher or lower than the first data point.)

5. Calculate the slope of the Dipole as, for example, $(Y_1-Y_2)/X$

Where;
Y1=first saturation in percent
Y2=second saturation in percent
X=the measurement interval of the Dipole in seconds 6. Identify the next consecutive data point along said waveform said next data point with the immediately preceding data point (i.e. the second data point of the first dipole) comprising the next Dipole and then;
   a. Define the next Dipole as positive when the next data point is higher then said preceding data point.
   b. Define the next Dipole as negative when the second data point is lower then said preceding data point.
   c. Define the next Dipole as neutral when the second data point is the same as said preceding data point.
7. Calculate the slope of the next Dipole.
8. Repeat steps 6 and 7 along said entire waveform (for example specifying each consecutive Dipole as Dipole $_{(1+Z)}$ where Z is equal to the number of preceding measured data points.)
9. Compare the polarity of each consecutive Dipole.
10. Define an Aggregate Dipole as two or more consecutive Dipoles of the same polarity
11. Calculate the slopes of all Aggregate Dipoles.
12. Define an Event as an Aggregate Dipole which includes the maximum number of Dipoles occurring consecutively with the same polarity. (A threshold number of dipoles or a threshold duration may be used to further define an event)
    a. Define the Event as a "Resaturation" when the slope of said Event is positive and the duration of said Event is greater than 5 seconds and less than 60 seconds.
    b. Define the Event as a "Desaturation" when the when the slope of said Event is negative and the duration of said Event is greater than 9 seconds and less than 160 seconds.
    c. Define the Event as a "Plateau" when the slope of said Event is zero.

(A threshold magnitude of increase or decrease in slope (e.g. greater than 0.2%/sec. or less than –0.2%/sec.) may be used to define when said slope is above or below a plateau range)

13. Calculate the mean slopes of all Events.
14. Define a negative oscillation as a Desaturation followed by a Resaturation within a specific interval of less than 15 seconds and calculate the duration of said oscillation defined by the beginning of said Desaturation to the end of said Resaturation.
15. Define a positive oscillation as a Resaturation followed by a Desaturation within a specific interval of less than 60 seconds and calculate the duration of said oscillation defined by the beginning of said Resaturation to the end of said Desaturation.
16. Define a Bipolar Oscillation as a Negative Oscillation followed by a Positive Oscillation wherein the desaturation of said Positive Oscillation occurs within 60 seconds of said Negative Oscillation.
17. Define a Coupled Oscillation as two consecutive Negative Oscillations wherein the desaturation of the second Negative Oscillation occurs within 60 seconds of the end of the Resaturation of the first Negative Oscillation.
18. Compare the slopes of each consecutive Desaturation with a first range of slopes consistent with sleep apnea with a range of slopes consistent with sleep apnea.
19. Compare the slopes of each consecutive Resaturation with a second range of slopes consistent with sleep apnea.
20. Define a cluster as at least 3 consecutive coupled oscillations wherein at least 75% of said slopes fall within said specific respective ranges.
21. Diagnose Sleep Apnea if a cluster is identified having at least 4 said consecutive coupled oscillations or if at least two clusters are identified.

Figure 14:
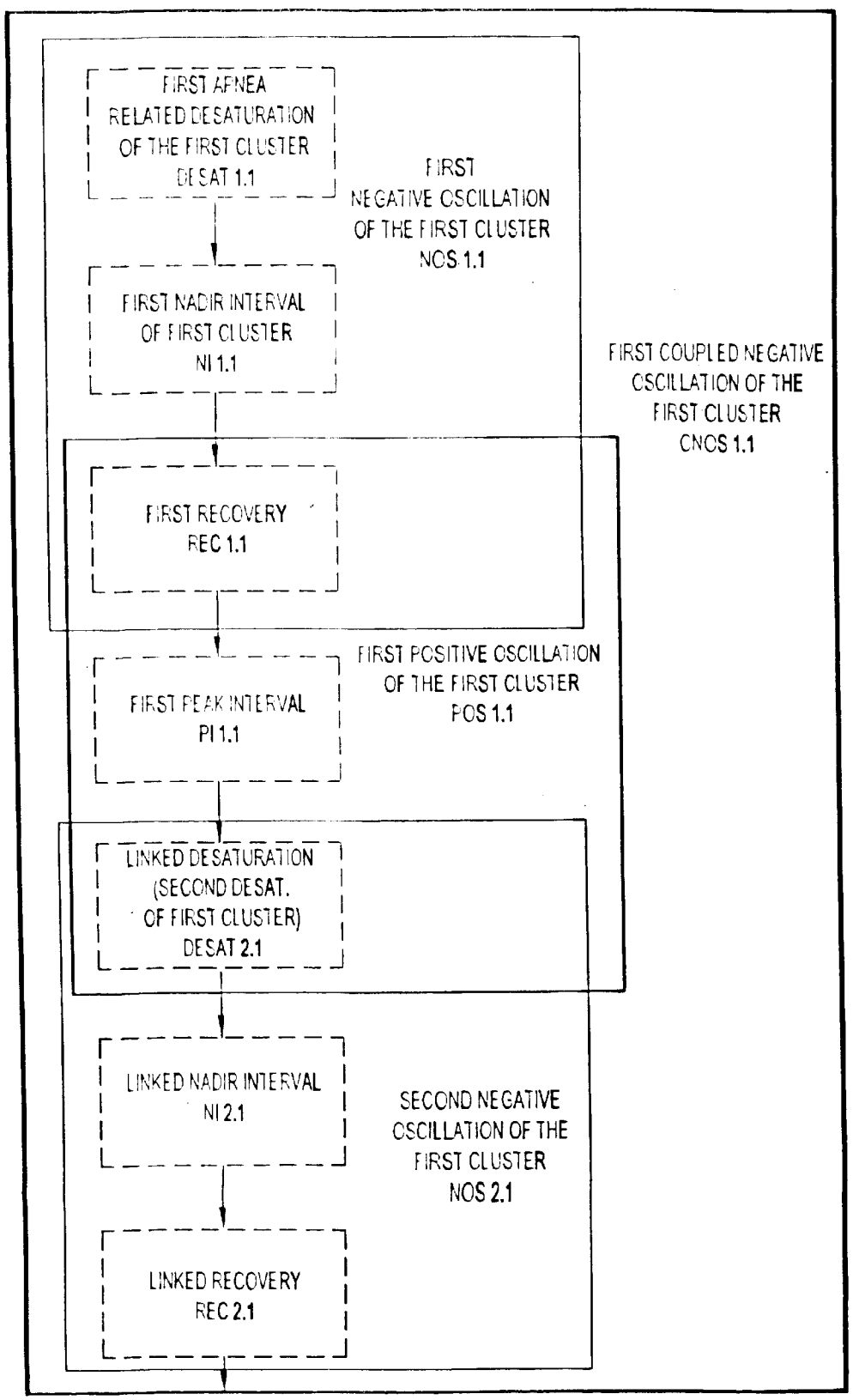
FIG. 14 shows a schematic illustration of the sequential building of objects according to the present invention.

FIG. 14 illustrates mapping of an object oriented analysis system using a sequentially building process through the identification (by comparison with predetermined ranges of slopes and intervals) of each basic object and then by the addition of this basic object to the preceding object if said identified basic object occurs within a predetermined interval and in a predetermined order of sequence. In this one preferred embodiment the property types of specific components of the oxygen saturation time waveform are defined such that the specific components are treated each as an individual object for both the purpose of identification and comparison. FIG. 15a and FIG. 15b provides an illustrative procedural embodiment written in visual basic version 5 which iterates through a set of consecutive saturation points and identifies and creates objects including dipoles, events, oscillations, and coupled oscillations as a function of the specific parameters discussed supra. As illustrated in FIG. 14, each object is defined by one or more parameters which may have a specific range. For example, the first apnea related desaturation of the first cluster (which is designated DESAT 1.1) must fall within a specific range of slopes and duration to receive that designation, (these ranges have been discussed earlier) and can be defined as having a beginning and an end (for example as a function a maximum duration and of said slope range). In another example, the first nadir interval (NI 1.1)—defined as the interval from the end of DESAT 1.1 and the onset of the first recovery (REC 1.1), is defined as falling within a specific maximum duration (such as within 15 seconds). While the first peak interval (PI 1.1)—the interval between the end of REC 1.1 and the beginning of the second desaturation (DESAT 2.1) can also be defined as falling within a specific maximum (such as within 90 seconds). The basic objects must occur within a limited time interval of each other and must occur in a specific order to function as the appropriate basic objects (building blocks) for the derivation of more complex objects.

In this analytic embodiment each frequency measurement derived from each object (which can be designated as f Object x.x) is said to represent a parallel object. (e.g. f NOS 1.1 is an object having a parallel relationship to the object NOS 1.1 and can for example be compared and should be similar to object f NOS 1.2). In the analysis, the complex objects are built from the basic objects and entire waveform may be scanned for each basic and complex object and then the objects compared. In this way both the identification of each object and the comparison of each object with other objects contributes to increased specificity in the diagnosis of sleep apnea.

When a microphone and audioprocessor are included, as shown in FIG. 1, each dipole can be coupled for analysis and comparison with other dipoles to the digital sound occuring within the dipole time interval. In this situation the each specific dipole object or a each more complex object (such as a negative oscillation) will have the additional property attributes of digital sound such as the presence of sound, the absence of sound, frequency, volume, and quality. Both absolute (presence or absence of sound over background) timing and frequency timing is an important feature which can be linked to more complex objects of longer duration. As previously discussed, the frequency of sound is different with different portions of the sleep apnea cycle. After adjusting for the delay (as will be discussed) the first portion of a positive oscillation is associated with the high frequency sounds of recovery related hyperventilation through a widely open airway, the second portion (including a portion of the peak interval) is associated with the low frequency sounds of vibrations generated by partially occluded upper airway, and the terminal portion is associated with the absolute absence of sound (over background noise). Each timed saturation event object can be evaluated with its coupled sound (which sound can be initially transformed into the frequency domain).

A delay (as is known in the art) is associated with the response of the pulse oximeter and since this delay is in part a function of the body part chosen for probe placement (e.g. the delay is longer for the toe than the finger). This delay can be factored into the matching of specific timed oxygen saturation objects so that each object is matched more accurately with the sound occurring in association with the specific event or object. For example a patient can demonstrate a "idesaturation delay" with a Ohmeda 3760 oximeter of 75 seconds from the onset of apnea (cessation of sound) to the beginning of the desaturation event whereas the "resaturation delay" from onset of airway opening and hyperventilation (initial high frequency sound) to the onset of the resaturation event in the same patient can be 50 seconds. The difference between these two delays is a function of the presence of oxygen storage in the lungs and the venous blood as previously discussed and the loss of difference between the desaturation delay and the resaturation delay is evidence of low oxygen stores at apnea onset For example the desaturation delay interval may fall during a cluster of severe apneas.

In this way the time of onset of apnea can be determined by the identification of the point at which cessation of low frequency sound occurred wherein said cessation was followed within an acceptable desaturation delay interval (for example between 40–90 seconds) by a desaturation event meeting the characteristics of a sleep apnea related desaturation. The time point of recovery can be identified by the point of onset of high frequency sound wherein said point follows said cessation of low frequency sound within a finite period (for example less than 3.5 minutes) and wherein said point of onset is followed within an acceptable resaturation delay interval (for example between 30–60 seconds) by a saturation event meeting the characteristics of a sleep apnea related resaturation. Apnea duration by sound index may then be calculated as the time point of low frequency cessation less the time point of high frequency onset. As described above the combination of sound characteristics coupled with specific identified, slope defined, objects along the oxygen saturation waveform provides enhanced sleep apnea diagnostic capability with only a single connection to the patient during sleep.

In another preferred embodiment the identification of desaturation regularity and frequency is used to identify the presence of a cluster. The waveform is scanned by a method for identifying a desaturation event (as by one of the previously described methods). The presence of a cluster of desaturations is identified wherein the interval between consecutive desaturations is regular and falls within a maximum range (such as 210 seconds). The mean interval between desaturations and the desaturation event frequency for each clustering of desaturations is identified. The presence of irregular occurring clusters of regular desaturations has similar diagnostic relevance to the identification of irregular clusters of regular oscillations but with less specificity.

In one preferred embodiment, the sleep diagnostic system described above can be designed so that it can be coupled with a conventional airflow measurement device (such as a spirometer) to enhance the value to the primary care physician or lung specialist in sleep diagnosis. It is useful to know the minute ventilation (liters of air inhaled and exhaled by the lungs per minute) which relates to a given patient's arterial oxygen saturation. In addition, and perhaps more importantly, it is useful to know the magnitude and rate of change in oxygen saturation induced by a given change in minute ventilation or, alternatively, the magnitude of change in minute ventilation required to achieve a given change in oxygen saturation. Furthermore, a patients tolerance during the awake state for a given fall in level of ventilation or oxygen saturation can provide evidence in support of the presence of sleep disordered breathing. For these purposes the sleep apnea diagnostic system described above can be enhanced for use in the physicians office by providing with the microprocessor a connection to a the output of a conventional spirometer having a pnuemotach for measuring minute ventilation. The microprocessor includes an algorithm to integrate the oximetry output with the spirometry output to generate the timed oxygen saturation waveform coupled to a timed minute ventilation waveform for comparisons between the absolute values and slopes of the oxygen saturation with the minute ventilation.

Patients with hypoventilation syndromes often have modestly increased arterial partial pressures of carbon dioxide during the day. In such patients arterial oxygen saturation may be normal (e.g. 91–93%) but because the carbon dioxide related drive to breathe is reduced in these patients it is often easy for these patients to volitionally hypoventilate while awake. Since these patients often have normal dead space ventilation and live near the steeper portion of the oxyhemoglobin dissociation curve, a reduction in minute ventilation by 50% results in a characteristic fall in oxygen saturation which is not easily achieved by a patient with a normal drive to ventilate. Furthermore patients with intrinsic lung disease may have high dead space ventilation such that marked changes in ventilation have little effect on oxygen saturation. Using the combined device, the a timed fall can be induced in several ways:

The patient is allowed to lie in a recumbent position for 5 minutes. An oximeter is attached to the patient, a pneumotachometer is placed in the patients mouth (a nose clip is applied) and the patient is told to breathe normally through the pneumotachometer until a stable baseline minute ventilation is identified (this can be automatically identified by the microprocessor). Once this has been completed one of the following maneuvers can be utilized.

1. The patient is instructed to hyperventilate (as to a certain minute ventilation threshold which may for example be 5 times the baseline level) for 20–30 seconds and then the patient is told to rest (with the pnuemotach in place). Patients with a reduced drive to ventilate will often demonstrate marked overshoot in the post hyperventilatory period with a marked fall in minute ventilation and a brisk fall in oxygen saturation to levels below the prehyperventilation baseline whereas normal patients generally do not demonstrate significant overshoot in the awake state. A coupled, timed arterial oxygen saturation and minute ventilation waveform is recorded and plotted for the entire maneuver and the slope of the post hyperventilatory fall in saturation is calculated. A fall of more than 3% below prehyperventilation baseline is indicative of reduced ventilatory drive and suggestive of a high risk of sleep disordered breathing.

2. The patient is instructed to slow breathing down to a threshold level (e.g. 50% of the baseline level). Patients with reduced drive will tolerate lower minute ventilation during wakefulness thereby resulting in oxygen desaturation generally below 90%. A fall in oxygen saturation to levels below 90% without an extreme sense of shortness of breath is suggestive of reduced ventilatory drive and suggestive of a high risk of sleep disordered breathing.

3. The patient is instructed to hyperventilate (as to a certain minute ventilation threshold which may for example be 5 times the baseline level) for 5 seconds and then the patient is told to rest (with the pnuemotach in place) for 15–25 seconds and then the cycle is repeated up to 5 times. In a manner similar to the single prolonged hyperventilation described above, patients with a reduced drive to ventilate will often demonstrate marked overshoot in each post hyperventilatory period with a marked fall in minute ventilation and a brisk fall in oxygen saturation to levels below the pre hyperventilation baseline (greater than 3% below baseline) whereas normal patients generally do not demonstrate significant overshoot in the awake state. A coupled, timed arterial oxygen saturation and minute ventilation waveform is recorded and plotted for the entire maneuver and the slope of the post hyperventilatory fall in saturation is calculated. An abnormal arterial saturation curve indicative of reduced ventilatory drive will demonstrate a cyclic pattern with slopes similar in desaturation and resaturation to that describe above in sleep apnea, this is suggestive of a high risk of sleep disordered breathing.

4. The patient is instructed to exhale completely and hold his or her breath as long as possible, then take 4 deep breaths quickly and repeat the exhale-breath holding-hyperventilation cycle for 4–5 times. A pattern of cyclic desaturation similar to that occurring in sleep apnea can occur in normal individuals with a highly motivated breath-holder but rapid desaturation slopes and tolerance to marked falls in oxygen saturation are suggestive of a high risk of sleep disordered breathing. Patients with an early and brisk fall in oxygen saturation with breath holding have either a low residual volume and/or a low mixed venous oxygen saturation. Especially in the non-obese, this simple, inexpensive, and noninivasive maneuver can provide a clue to the presence of cardiac disease especially if a biphasic (initial rapid desaturation slope and later slower desaturation slope) fall in oxygen saturation is noted (as discussed earlier for sleep apnea).

The following are examples of clinically useful indices which can be calculated by the described embodiment (the corresponding time interval for each of these indices is adjusted for the delay in oxygen uptake and transmission into oxygen saturation data by the pulse oximeter as is known in the art):

1. The saturation to ventilation index $$(SaO2_{ta}-84)/Ve_t$$

Where;
Vet=the average minute ventilation during a time interval and,
$SaO2_{ta}$=the average arterial saturation during the corresponding time interval The higher this index the greater the probability of a hypoventilation disorder and attendant sleep disordered breathing (As shown, this index is only for saturations of 85 or above)

2. The delta saturation to delta ventilation index $$dSaO2_{ta}/dVe_t \text{(change in \% saturation/change in minute ventilation)}$$

Where;

Ve$_t$=the average change in minute ventilation during a time interval (either increase or decrease) and, SaO2$_{ta}$=the average change in arterial saturation during the corresponding time interval Patients with intrinsic lung disease have a lower index than normal. This index helps differentiate whether a low baseline saturation is due to hypoventilation or intrinsic lung disease.

Figure 16:
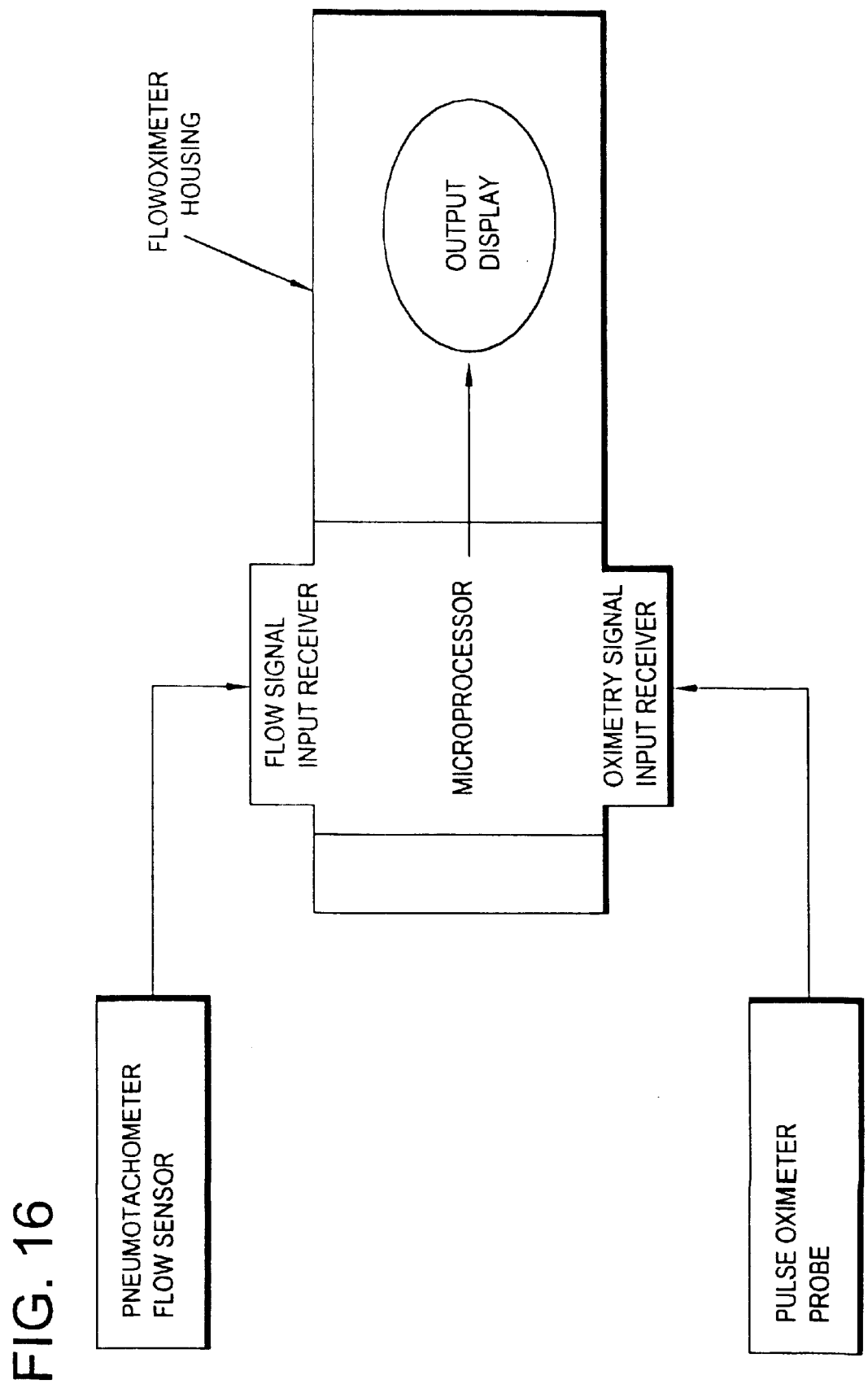
FIG. 16 is a schematic illustration of one preferred embodiment of a portable minute volume indexing pulse oximeter according to the present invention.
Figure 17:
FIG. 17 is a schematic illustration of a spirometer coupled to a pulse oximeter for generating a ventilation indexed pulse oximetry value according to the present invention.

FIG. 16 illustrates a preferred compact single unit configuration which the inventor calls "portable flowoximetry" which allows portable determination of the above parameters. This configuration is achieved by:

1. Combining an oximeter and spirometer into a single compact casing which can be easily carried to the bedside.
2. Attaching a pulse oximeter probe and a flow sensor to the integrated pulse oximeter.
3. Using the microprocessor, integrating the timed oximetry signal and timed exhaled (or inhaled) gas flow (an adjustment may be made for the oximetry signal delay as described supra.)
4. providing output of oxygen saturation indexed or the timed or averaged exhaled volume FIG. 17 illustrates an embodiment for office use. The configuration and operation is achieved by:

1. providing an oximetry signal input receiver as part of an office spirometer and then,
2. using the microprocessor, integrating the timed oximetry and timed flow (an adjustment may be made for the oximetry signal delay as described supra.)
3. providing output of oxygen saturation indexed for the timed or averaged exhaled volume.

Figure 18:
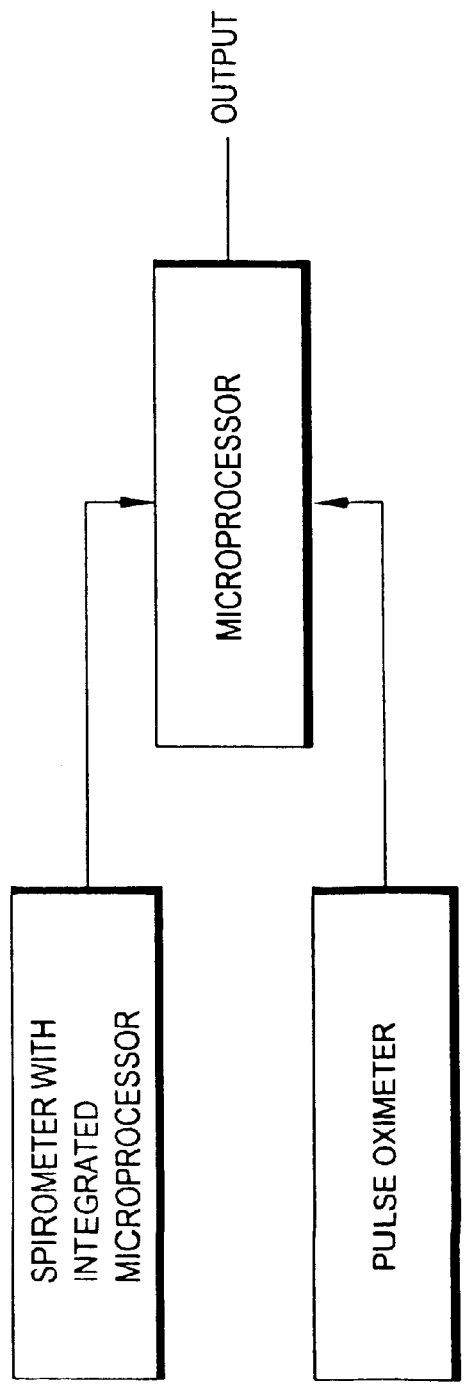
FIG. 18 is a schematic diagram of a microprocessor for coupling with a spirometer and a pulse oximeter for generating a ventilation indexed pulse oximetry value according to the present invention.

FIG. 18 illustrates an embodiment for use with existing oximeters and spirometers having output jacks which can be accessed for connection to a central microprocessor. The configuration and operation is achieved by:

1. connecting the output of an oximeter and the output of a spirometer to a microprocessor,
2. Using the microprocessor, integrating the timed oximetry flow (an adjustment may be made for the oximetry signal delay as described supra.)
3. Providing output of oxygen saturation indexed for the timed or averaged exhaled volume.

The previously described sleep apnea diagnostic system of the present inventor can be used to determine the severity of sleep apnea. Studies have demonstrated that the standard "apnea hypopnea index" which is calculated by counting the numbet of apneas and hypopneas and dividing by the number of hours of sleep is a poor indicator of disease severity. There has long been a critical need for a new method to assess severity and indeed ongoing studies sponsored by the National Institute of Health are attempting to identify the validity of the apnea hypopnea index and to identify a valid signal of disease severity. As discussed supra the cluster characteristics can be used to define severity. The present inventor has discovered a system and method, which can be used to enhance the determination of disease severity. In the presently preferred embodiment, this system and method determines a value indicative of the sufficiency of recovery associated with sequential apneas and uses at least this value to define the disease severity in sleep apnea.

It has been long believed that the number and duration of apneas determined the severity of disease. This basic concept seems intuitive. (i.e. If apnea are the detrimental events then it seems rational that the number and duration of the apneas would define severity). Perhaps because the severity issue seems so straightforward, the concept of severity as a function of enumeration of apneas has been promulgated for decades and represents the standard of severity assessment in modem sleep medicine. However, the present inventor noted that with respect to breath holding that severity cannot be determined by the number and longevity of the breath holdings or by the magnitude of arousals or oxygen desaturation associated with the breath holdings, but rather is uniquely dependent on the sufficiency of the recovery interval between breathholds. This is due to the fact that mammals (including humans) have an oxygen storage mechanism to protect against the stress of breathholding but this storage mechanism is readily depleted and must be repleted before the next breathhold. This means that, with respect to apnea, there is a unique and critical relationship between cardiovascular stress associated with the sequential breathholds which naturally occur as a part of a self propagating apnea cluster and the recovery interval between breathholds. Indeed, this "sufficiency of recovery" between apneas is defined by a critical interaction between the number of breathholds occurring in sequence, the longevity of the breatholds, and the recovery time between the breatholds. As discussed supra these relationships are provided by analyzing the apnea cluster waveform. The present inventor has proposed that the diving seal provides a reasonable analogy. The seal can dive very often and long without cardiovascular compromise as long as the animal has sufficient free breathing recovery intervals above water between dives. When this interval is limited the seal faces a serious cardiovascular threat if the dives are frequent and prolonged. Indeed, in the wild, the need for sufficient recovery interval is exploited in the interest of predation. It is this unique relationship between severity and the sufficiency of recovery between sequential apneas which the present inventor has utilized to provide a new system and method to determine the severity of sleep apnea.

Upon this discovery the present inventor designed a system and method of evaluating a patient with sleep apnea. The method includes identifying a plurality of sequential apneas, determining a value indicative of the sufficiency of recovery between the apneas, and determining the severity of sleep apnea based at least on said value. The value can be measurement such as the time interval or another measurement such as the relative amount of gas exhaled or inhaled from the mouth or nose between apneas. Both the interval time and the relative amount of gas exhaled can be used in combination and another value indicative of the sufficiency of recovery can be calculated using this combination as for example the product of the time and a measurement of the relative gas exhaled. The exhaled gas can be measured directly or inferred relative to a baseline using a flow sensor (as is known in the art). Another value indicative of the sufficiency of recovery is a measurement indicative of an oxygen saturation between apneas which can for example be expressed as the average oxygen saturation of the recovery interval. A presently preferred embodiment can include the steps of monitoring a patient to produce at least one timed waveform of at least one physiologic parameter. The physiologic parameters can include for example arterial oxygen saturation, the flow of gas at the nose and or mouth, (as can be measured by a thermister or a carbondioxide monitor as is known in the art), or chest wall movement. Then, the step of identifying all) along said waveform a first waveform variation indicative of an apnea, then identifying along said waveform a second waveform variation indicative of another apnea. then determining (as for example by measuring or calculating) the interval intermediate at least one portion of said first waveform variation and at least one portion of said second waveform, and finally assessing the severity of sleep apnea based on at least said determining.

An example of a waveform variation indicative of apnea is described supra for the oximetry waveform and can comprise a coupled desaturation and resaturation having characteristic slopes and occurring within a desaturation cluster as previously described. Preferably one portion of the first waveform variation corresponds to said one portion of the second waveform variation and it is further preferable that said one portion of the first waveform variation is substantially the last portion of said first waveform variation but the interval can extend into each waveform variation as is described below for the interval termed the oxygen repletion interval where a portion of the second waveform variation is incorporated into the intervening interval. One portion of the second waveform variation can be substantially the first portion of the second waveform variation.

The method can include identifying at least one cluster of waveform variations indicative of a corresponding cluster of apneas wherein said severity assessment or determining is based on the position of said waveform variations within said cluster relative to other waveform variations within said cluster. Alternatively or in combination a spatial cluster waveform pattern indicative of a spatial pattern of a corresponding cluster of apneas can be used to determine the spatial relationships of said waveform variations within said cluster waveform pattern to determine the severity of sleep apnea.

The device for determining the severity of sleep apnea can comprise a monitor such as an oximeter or flow sensor capable of generating a signal indicative of at least one physiologic parameter and a processor (such as an integrated computer or a separate lap top computer) capable of processing said signal, said processor can operate to generate a timed waveform of said parameter and to identify a plurality of sequential waveform variations indicative of a corresponding plurality of sequential apneas, the sequential waveform variations have temporal and spatial relationships between said waveform variations and along the waveform (as was discussed at length supra). The processor further can operate to determine at least one of said temporal and said spatial relationships and to display said result or determining so that said determining can be used to assess the severity of sleep apnea.

Importantly the method of determining the severity of sleep apnea can comprise the steps of identifying a plurality of sequential apneas having a spatial relationship to each other, determining said spatial relationship, and defining the severity of sleep apnea based on at least said determining. The spatial relationship can be defined by an object-oriented method as discussed supra or by other known graphical methods which include pattern recognition or graphical event recognition. Alternatively or in combination with the methods noted above, a method of determining the severity of sleep apnea can comprise steps of identifying a plurality of sequential apneas having a temporal relationship to each other, determining said temporal relationship, and defining the severity of sleep apnea based on at least said determining. The temporal relationship can be defined by an object-oriented method as discussed supra or by other known methods such as frequency analysis or graphical event recognition.

One preferred embodiment of a method to define the severity of sleep apnea is as follows:

Define a Desaturation Object as including two component objects:
1. An Initial Limb defined as that portion of the desaturation above a specific threshold saturation (e.g. to a sat. of 80%) or as a percentage of the total fall in saturation (e.g. Forty percent of the total fall).
2. A Terminal Limb defined as that portion of the desaturation remaining after he Initial Limb Define a Positive Oscillation as a Resaturation followed by a Desaturation within a specific interval of less than 60 seconds.

Within each cluster, define a Repletion Interval as an object including a Resaturation, a Plateau (the plateau may be absent t and an Initial Limb within a Positive Oscillation Note: By extending this calculation through the initial limb this calculation takes into account the effect of an increased initial portion of the subsequent desaturation slope on the oxygen availability during the recovery interval.

Calculate the average oxygen saturation during each Object as:

$$\overline{SaO2} = \frac{1}{n}\sum_{i=1}^{n} SaO2(i\Delta t)$$

Where: i=1 is the initial sample of the object, and i=1 is the final sample, and $\Delta t$ is the time interval between samples With the object oriented program previously described the average oxygen saturation can comprise a characteristic of an object and as such can be easily compared and plotted (for example, against duration of each object). This can for example, be applied to the repletion intervals within a given cluster. When plotted in this manner with saturation on the y-axis and time on the x-axis a grouping of repletion intervals within the left lower quadrant of the plot is indicative of cluster with a low mean or median recovery interval in association with a low means or median oxygen saturation during the recovery interval. This is generally indicative of more severe sleep apnea but the indicator of severity is further enhanced and improved by incorporating the duration of the adjacent apneas such as the immediately bracketing apneas into the plot or calculation. The microprocessor system described supra can be used to assess and graphically present a severity analysis and to calculate a severity index, which can be derived as follows in a presently preferred embodiment.

1. PROGRAM—identifies the object cluster as defined above
2. PROGRAM—calculates the following for each cluster object:
   1) Mean and median saturation (iterates through oxygen saturation values)
   2) Mean and median apnea and cluster duration
   3) Mean and median recovery interval (calculated as end of the nadir to onset of next desaturation.) and calculate avg. sat for each recovery interval and mean and median avg. saturations for said recovery intervals
   4) Mean and median maximum oxygen repletion interval (as mean recovery interval+40 percent of the next desaturation event) and calculate the avg. saturation and mean and median avg. saturations for this interval.
   5) Plot the distribution of the duration for each repletion interval (x-axis) with either the average saturation for each repletion interval (y-axis) or the average duration of the apneas before and after each repletion interval (y-axis) (For example the durations of the two apneas immediately before and two apneas immediately after the repletion interval divided by 4). This plot is performed for each cluster object and also performed as one plot in aggregate for all clusters.

6) Calculate the mean and median saturation of non clustered recording.

7) Calculate the time in minutes below 90%, 85%, 80%, and 70% during cluster objects and during recording time wherein said objects are not present. Plot this as a comparison bar graph side by side (non clustered bar for 90% adjacent clustered bar for 90% etc.) where the y axis is percent of total recording total recording time and again on another graph where the y axis is time in minutes (the length of the y axis is equal to the total recording time).

8) Plot total cluster time and total non cluster time on a separate graph.

9) Calculate a value of the sufficiency of recovery as a sleep apnea severity index tenued the "Oxygen Repletion Index" (ORI) as the product of Oxygen Saturation minus 80 and the repletion interval. The ORI is given in "Saturation Seconds". This can be calculated for each recovery interval and as a mean or median value for each cluster or portion of a cluster (such as a portion of a cluster having a greater apnea duration or a greater magnitude of desaturation) or for the entire night.

10) Calculated another value of the sufficiency of recovery as another sleep apnea severity index "Apnea Recovery Index" (ARI) as the quotient of the ORI and the mean duration of the apneas immediately bracketing each recovery interval. The ARI is given in "Saturation Seconds per Minute of Apniea". This also can be calculated for each recovery interval and/or as a mean or median value for each cluster or portion of a cluster (such as a portion of a cluster having a greater apnea duration or a greater magnitude of desaturation) or for the entire night.

Illustrative Examples of ORI and ARI Calculations

A mean repletion interval saturation of 90% and a Repletion interval of 20 seconds generates an ORI of 200 saturation seconds. If the bracketing apneas have a mean duration of two minutes this generates an ARI of 100 saturation seconds per minute of apnea indicating mild severity.

A mean repletion interval saturation of 85% and a Repletion interval of 20 seconds and a mean bracketing apnea duration of two minutes generates an ARI of 50 saturation seconds per minute of apnea indicating a greater degree of severity.

A mean repletion interval saturation of 82% and a Repletion interval of 20 seconds and a mean bracketing apnea duration of two minutes generates an ARI of 20 saturation seconds per minute of apnea indicating very severe disease.

A mean saturation of the repletion interval saturation of 78% and a Repletion interval of 20 seconds and a mean bracketing apnea duration of two minutes generates an ARI of −80 saturation seconds per minute of apnea. (note here that in the event that the ORI is a negative number the mean duration of the bracketing apneas is multiplied times the ORI to generate the ARI). This level of ARI is indicative of profound life threatening severity.

Note: Saturations below 80% will generate a negative ORI. A lower negative ORI associated with increasing repletion times accounts for the fact that a long repletion time is actually reflects greater severity when the mean saturation of the repletion interval is profoundly decreased since this indicates profound disease.

Alternatively, the index can be based on the recovery interval time and the duration of the bracketing apneas without consideration of the oxygen saturation. These basic severity indices would be given in seconds per minute of apnea. Such severity indices are easy for physicians to understand. For the purpose of defining the relative potential for reduced oxygen delivery in the presence of critical vascular stenosis these indices can be weighted to maximize the effect of lower saturation on oxygen delivery during the repletion interval. Additional weighting can be provided to incorporate the average duration of the clusters in combination with the mean recovery interval within clusters which is another important value indicating sleep apnea severity.

It is clear that alternative severity indices can be provided within the scope of the present invention. For example the number of breaths exhaled or inhaled between apneas can be used and indexed in combination with the mean duration of the bracketing apneas. Also a wide range of alternative aggregate severity indices of obstructive sleep apnea can be provided utilizing the system and method of the present invention which incorporate measurements or identification of events or deflections along the waveform which correlate with the sufficiency of the recovery intervals. Such severity indices can include in combination with the repletion intervals, or recovery intervals, the enumeration or frequency evaluation of identified events or measurements indicative of apnea along the waveform or can include waveform pattern identification which provides for the identification of grouped or closely spaced waveform deflections which correlate with grouped or closely spaced apneas or apnea clusters having limited recovery intervals. As has been shown by this teaching, with such a grouping, the limitation of the recovery interval may be inferred, for example, by a particular waveform pattern of tightly grouped waveforms of high amplitude deflections.

In the preferred embodiment, severity is defined as inversely proportional to the duration of the repletion intervals and the oxygen saturation of the repletion interval within the clusters and directly proportional to the duration of the apneas within the cluster. In addition, the number of breaths, the relative magnitude of the breaths, the slope of the initial 50% of the descending limbs of the desaturations within the cluster, and the duration of the clusters may be all be incorporated to produce an aggregate index. Within the scope of this teaching, alternative intervals can be used in place of the illustrative repletion intervals and recovery intervals described herein and further additional intervals may be learned during the application of this teaching to clinical practice.

Although the presently preferred system and method for identifying the presence of sleep apnea and for determining the severity of sleep apnea have been described, it will be obvious to those skilled in the art that various modifications and changes may be made without departing from the scope of the invention. Therefore the claims are intended to include all such changes and modifications that fall within the true spirit and scope of the invention.

What is claimed is:

1. A device for determining the respiratory status of a patient, the device comprising:
   a ventilation indexing oximeter including:
   a. a ventilation measurement device for generating a first result indicative of the volume of at least one gas ventilated as a function of time, b. an oximeter for generating a second result indicative of the oxygen saturation of human blood, and c. a microprocessor programmed for comparing the first result with the second result to generate a third result indicative of both the first result and the second result.

2. The device of claim 1 wherein the ventilation measuring device comprises a flow sensor capable of determining the minute ventilation of a patient.

3. The device of claim 2 wherein the ventilation measuring device comprises pneumotachometer.

4. The device of claim 1 wherein the oximeter is a pulse oximeter.

5. The device of claim 1 wherein the first result is total volume of substantially all gasses ventilated by the patient per unit of time.

6. The device of claim 1 wherein the first result is determined for a first time interval.

7. The device of claim 6 wherein the second result is determined for a second time interval.

8. The device of claim 7 wherein the second time interval commences after the onset of the first time interval.

9. The device of claim 8 wherein the second result is the average oxygen saturation within the time interval.

10. The device of claim 7 wherein the second time interval is shorter than the first time interval.

11. The device of claim 7 wherein the second result is the average oxygen saturation within the time interval.

12. The device of claim 7 wherein the third result is a calculated index of the first result and the second result.

13. The device of claim 6 wherein the first time interval is sufficient for the patient's respiratory status to become stabilized.

14. The device of claim 6 wherein the first result is the average minute ventilation within the time interval.

15. The device of claim 1 wherein the first result is the average minute ventilation.

16. The device of claim 1 wherein the second result is the average oxygen saturation.

17. The device of claim 1 wherein the third result is a calculated index of the first result and the second result.

18. The device of claim 1 further including a housing for enclosing at least the microprocessor and including at least one port for receiving input from at least one of the oximeter and the flow sensor, the housing being sized and configured to be hand held and carried to a patient's bedside.

19. A method of assessing gas exchange of the respiratory system of a patient, the method comprising:

a. using a flow measuring device, measuring a volume of at least one ventilated gas over a first time interval to derive a first result, the result being substantially equal to the volume of the at least one gas ventilated by the patient during the first interval, b. using an oximeter, measuring the oxygen saturation of arterial blood over a second time interval to derive a second result, the second result corresponding to the oxygen saturation of arterial blood induced by the first result; and c. using a computer, comparing the first result with the second result to derive a third result indicative of both the second result and the first result.

20. The method of claim 19 wherein the first result is at least the volume of ventilation of substantially all ventilated gasses per unit of time during the first time interval.

21. The method of claim 20 wherein the second result is at least the average oxygen saturation of arterial blood as measured by the oximeter during the second time interval.

22. The method of claim 21 wherein the comparing comprises calculating an index indicative at least of both the first result and the second result.

23. The method of claim 20 wherein the first result further comprises at least a magnitude of change in minute ventilation.

24. The method of claim 19 wherein the second result is at least the average oxygen saturation of arterial blood as measured by the oximeter during the second time interval.

25. The method of claim 19 wherein the comparing comprises calculating an index indicative at least of both the first result and the second result.

26. The method of claim 19 wherein the comparing comprises the computer mathematically comparing at least the first result with the second result.

27. The method of claim 19 wherein the first result comprises at least a magnitude of change in minute ventilation.

28. The method of claim 27 wherein the first result further comprises at least a rate of change in minute ventilation.

29. The method of claim 27 wherein the second result comprises at least a magnitude of change in oxygen saturation.

30. The method of claim 29 wherein the second result further comprises at least a rate of change in oxygen saturation.

31. The method of claim 29 wherein the comparing comprises calculating an index indicative at least of both the first result and the second result.

32. The method of claim 19 wherein the first result comprises at least a rate of change in minute ventilation.

33. The method of claim 32 wherein the second result comprises at least a rate of change in oxygen saturation.

34. The method of claim 33 wherein the comparing comprises calculating an index indicative at least of both the first result and the second result.

35. The method of claim 32 wherein the second result comprises at least a rate of change in oxygen saturation.

* * * * *

UNITED STATES PATENT AND TRADEMARK OFFICE
CERTIFICATE OF CORRECTION

PATENT NO. : 6,342,039 B1  Page 1 of 1
APPLICATION NO. : 09/409264
DATED : January 29, 2002
INVENTOR(S) : Lawrence A. Lynn et al.

It is certified that error appears in the above-identified patent and that said Letters Patent is hereby corrected as shown below:

Title Page

Item [63], Related U.S. Application Data, should be corrected to read as follows:

Continuation-in-part of Application No. 09/115,226, filed on July 14, 1998, now Pat. No. 6,223,064 issued April 24, 2001, which is a continuation-in-part of Application No. 08/789,460, filed on January 27, 1997, which is a continuation of Application No. 08/391,881 filed on February 21, 1995, now Pat. No. 5,605,151, which is a continuation of application No. 08/151/901, filed on November 15, 1993, now Pat. No. 5,398,682, which is a continuation-in-part of Application No. 08/931,976, filed on August 19, 1992, now abandoned.

Signed and Sealed this

Twenty-second Day of May, 2007

JON W. DUDAS
*Director of the United States Patent and Trademark Office*